US011939560B2

(12) United States Patent
Magdesian et al.

(10) Patent No.: US 11,939,560 B2
(45) Date of Patent: *Mar. 26, 2024

(54) MICROFLUIDIC CELL CULTURE SYSTEMS

(71) Applicant: 9493662 Canada Inc., Quebec (CA)

(72) Inventors: Margaret Haiganouch Magdesian, Quebec (CA); Peter Thostrup, Viby J (DK)

(73) Assignee: 9493662 Canada Inc., Montreal (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/691,599

(22) Filed: Mar. 10, 2022

(65) Prior Publication Data

US 2022/0195365 A1    Jun. 23, 2022

Related U.S. Application Data

(63) Continuation of application No. 14/909,061, filed as application No. PCT/CA2014/000589 on Jul. 29, 2014, now Pat. No. 11,293,001.

(Continued)

(51) Int. Cl.
*C12M 3/06* (2006.01)
*B01L 3/00* (2006.01)
(Continued)

(52) U.S. Cl.
CPC ......... *C12M 23/16* (2013.01); *B01L 3/50255* (2013.01); *B01L 3/502715* (2013.01);
(Continued)

(58) Field of Classification Search
CPC ...... B01L 3/00; B01L 3/50255; B01L 3/5027; B01L 3/502761; B01L 3/502769;
(Continued)

(56) References Cited

U.S. PATENT DOCUMENTS

2011/0306041 A1* 12/2011 Viovy ................. C12N 5/0619
435/7.1

* cited by examiner

*Primary Examiner* — Dean Kwak
(74) *Attorney, Agent, or Firm* — Bell & Manning, LLC

(57) ABSTRACT

As with many human physiological systems, issues within the central nervous system can arise for individuals leading to a variety of neurological disorders including, but not limited to, Charcot-Marie-Tooth disease, Alzheimer' disease, Parkinson's disease, multiple sclerosis, myasthenia gravis, demyelination, and axonal degeneration. However, culture devices presently provide researchers with limitations in their research. Embodiments of the invention aims to address these various limitations and allow studies, methods and screenings which cannot be performed with prior art culture devices. These include reducing manufacturing complexity, volumes of pharmaceuticals and cells required, allowing use in fields other than neurobiology, improved adhesion within the desired micro-channel regions of the devices, and increasing cell survival in cultures. Accordingly, microfluidic devices comprising a connecting chamber and micro-channel having the same depth which prevents hydrostatic pressure, end walls of the connecting chamber and micro-channel arrays having a high angle relative to the fluid flow direction for supporting culturing and topside of the connecting chamber that has been profiled in order to improve the adhesion of cells is provided.

12 Claims, 19 Drawing Sheets

Related U.S. Application Data

(60) Provisional application No. 62/013,746, filed on Jun. 18, 2014, provisional application No. 61/859,318, filed on Jul. 29, 2013.

(51) Int. Cl.
  *C12M 1/00* (2006.01)
  *C12M 1/12* (2006.01)
  *C12M 1/34* (2006.01)

(52) U.S. Cl.
  CPC ............ *C12M 23/34* (2013.01); *C12M 25/06* (2013.01); *C12M 41/46* (2013.01); *B01L 2200/0642* (2013.01); *B01L 2200/0647* (2013.01)

(58) Field of Classification Search
  CPC ......... B01L 3/50857; B01L 2200/0642; B01L 2200/0647; B01L 2300/0816; B01L 2300/0867; B01L 3/502715; B01L 2200/16; B01L 2300/087; B01L 3/502746; B01L 2300/0851; C12M 23/16; C12M 23/34; C12M 25/06; C12M 41/46; C12M 47/04; G01N 15/1484; G01N 2021/7709
  USPC .......................................... 422/502, 503, 73
  See application file for complete search history.

Figure 17
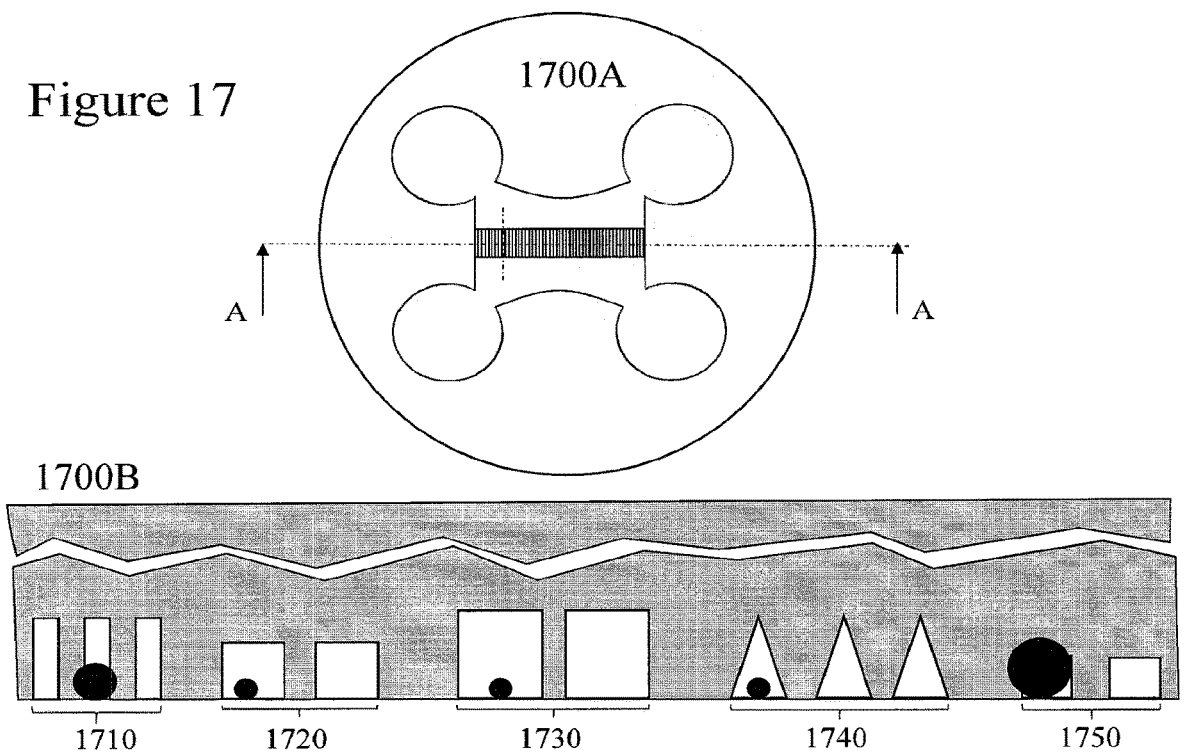
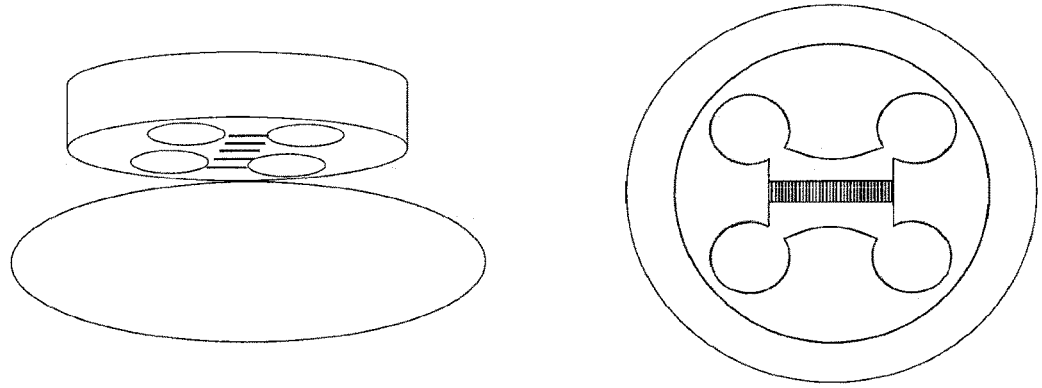
Figure 18

MICROFLUIDIC CELL CULTURE SYSTEMS

CROSS-REFERENCE TO RELATED APPLICATIONS

This application is a continuation application of U.S. patent application Ser. No. 14/909,061, filed Jan. 29, 2016, which is a U.S. National Phase Entry application that claims the priority benefit of International Application PCT/CA2014/000589 filed on Jul. 29, 2014 which claims the benefit of priority from U.S. Provisional Patent Application Ser. No. 61/859,318 entitled "Microfluidic Chambers" filed Jul. 29, 2013 and from U.S. Provisional Patent Application Ser. No. 62/013,746 filed Jun. 18, 2014 entitled "Microfluidic Chambers."

FIELD OF THE INVENTION

This invention relates to cell culture systems and more specifically to microfabricated, microfluidic culture systems for neurological research.

BACKGROUND OF THE INVENTION

Biological systems vary from the very simple to the incredibly complex. Amongst the many neurological systems within animals and humans the nervous system is the part that coordinates its voluntary and involuntary actions and transmits signals between different parts of its body. It consists of two main parts, the central nervous system (CNS) and the peripheral nervous system (PNS). The CNS contains the brain and spinal cord whereas the PNS consists mainly of nerves, which are enclosed bundles of the long fibers or axons, which connect the CNS to every other part of the body. The PNS includes motor neurons, mediating voluntary movement; the autonomic nervous system, comprising the sympathetic nervous system and the parasympathetic nervous system, which regulate involuntary functions, and the enteric nervous system, which functions to control the gastrointestinal system.

At the cellular level, the nervous system is defined by the presence of neurons, also known as "nerve cells". Neurons have special structures that allow them to send signals rapidly and precisely to other cells in the form of electrochemical waves traveling along thin fibers, referred to as axons, which cause chemicals, referred to as neurotransmitters, to be released at junctions, the synapses. It is the connections between neurons that form neural circuits and also neural networks that generate an organism's perception of the world and determine its behavior. The CNS of a human is estimated to comprise approximately 85 billion neurons, split approximately 20% and 80% between the cerebral cortex and the cerebellum.

As with many human physiological systems issue within the CNS can arise for individuals leading to a variety of neurological disorders including, but not limited to, Charcot-Marie-Tooth disease, Alzheimer' disease, Parkinson's disease, multiple sclerosis, myasthenia gravis, demyelination, and axonal degeneration. In many instances, these neurological issues arise in the elderly and our increased lifespan in the past two hundred years has made such issues evident and increasingly prevalent. Even in the period 1950-2010 life expectancy in Europe and North America is increased from 65 to nearly 80. In Asia it has increased from 40 to nearly 70. It is estimated that by 2050 1 in every 85 people globally will have Alzheimer's, or approximately 110 million people using the United Nation's world population estimate for 2050. Parkinson's by contrast is estimated to be 1 in every 300 people adding another approximately 30 million suffers in 2050.

Accordingly, neurological research is extremely important in order to either establish medical and/or pharmaceutical regimens for patients to mitigate/delay its effects to minimize financial burden on national health budgets and/or seek lifestyle, environmental, and/or pharmaceutical factors or adjustments that reduce, delay, or remove it's occurrence and impact to individuals. Cultures of disassociated cells make it possible for researchers to describe in much greater detail the neurological systems being studied and accordingly today many laboratories perform neuronal cultures. Traditionally, these neuron cultures were carried out within dishes or culture wells and have allowed significant research in the study of neurodegenerative diseases such as Alzheimer's disease, Huntington's disease, Creutzfeldt-Jakob disease, etc., but also in developmental biology for the understanding of molecular and cellular mechanisms of neuronal differentiation.

However, in these systems, the neuronal connections are made randomly and it is impossible to reconstitute therein an architecture similar to those that are found in vivo. Accordingly, whilst cell culture methods are a commonly used research technique to provide systematic controlled manipulation of growth conditions cells in many instances with neurons, synapses, and axons the dominant prior art methodologies that expose the entire cell to the same conditions are not always beneficial. Some cells can be asymmetrical and have regions that are specialized. Neurons, for example, are polarized and have many processes that extend over relatively long distances (e.g., axons). Accordingly, it would be beneficial to provide researchers, clinicians, etc. with microenvironments at a cellular level.

The ability to control fluidic and surface properties at the micron-scale, appropriate for cell biology, using microfabrication processes also provides new opportunities for investigating fundamental biological processes. A researcher may, for instance, selectively isolate and treat specialized portions or domains of the cell. The researcher can direct the sites of neuronal attachment and the orientation and length of neurite outgrowth by micropatterning techniques such as microcontact printing. Secondly, by maintaining fluidically isolated domains within the culture area researchers can deliver a series of positive or negative stimuli to the soma, axons or dendrites. As neurons represent an excellent cell type to illustrate these concepts and will the basis of many such experiments the inventors have therefore used them as the basis for experimental verification of their microfabricated microfluidic cellular culture concept. Those of ordinary skill in the art, however, will recognize that the methods and systems according to embodiments of the invention will have applicability to other types of cells or biological type applications.

Accordingly, embodiments of the invention are beneficially directed to a microfabricated microfluidic cellular system which combines micro-fabrication techniques for low cost, high volume, small footprint, systems together with low volume microfluidics and surface micropatterning techniques to create multi-compartment neuronal culturing devices. Microfluidics is increasingly the tool of choice for cell biology, and in particular for neurosciences. In WO/2004/034016 "Microfluidic Multi-Compartment Device for Neuroscience Research" by Jeon et al. and U.S. Pat. No. 7,419,822 entitled "A Microfluidic Device for Enabling Fluidic Isolation among Interconnected Compartments within the Apparatus and Methods relating to the same"; a microfluidic circuit configuration which makes it possible to isolate the soma of neurons from their axon. These structures being derived from the much earlier studies by Campenot in "Local Control of Neurite Development by Nerve Growth Factor" (Proc. Natl. Acad. Sci., Vol. 74(10), pp. 4516-4519]). Whilst suitable for studies of the neurons of the central nervous system (CNS) in vitro the method relies upon the fact that the diffusion times within the micro-channels are long, which makes it possible to treat the distal and somatic compartments separately.

In order to address this within the prior art compensation has been provided by imposing a pressure differential which is easily achieved. For example, it is merely sufficient to place a larger volume of liquid into a reservoir of one of the compartments in order to generate a hydrostatic pressure differential between the different compartments. Examples of such prior art include Jeon et al. in WO/2006/037033 entitled "A Micro-Fluidic Device for Enabling the Controlled Growth of Cells" and US 2008/0,257,735 entitled "Microfluidic Device for Enabling the Controlled Growth of Cells and Methods Relating to same." Viovy et al. in US 2011/0,306,041 entitled "Device for Cell Culture" sought to extend these concepts to neural networks and more complex structures. Devices according to U.S. Pat. No. 7,419,822 are currently commercially offered by Xona Microfluidics manufactured in polydimethylsiloxane (PMDS).

However, these devices still present researchers with limitations and accordingly, the present invention aims, inter alia, to address these various limitations and allow studies, methods and screenings which cannot be performed with the current prior art devices. These include reducing manufacturing complexity, volumes of pharmaceuticals and cells required, allowing use in fields other than neurobiology, improved adhesion within the desired micro-channel regions of the devices, compatibility with standard microscopes, enabling growth of axons longer than 1 mm, neutronal survival for extended periods of more than 14 days allowing synaptic imaging, and coating of structures with biologically relevant materials.

Other aspects and features of the present invention will become apparent to those ordinarily skilled in the art upon review of the following description of specific embodiments of the invention in conjunction with the accompanying figures.

SUMMARY OF THE INVENTION

It is an object of the present invention to mitigate limitations in the prior art relating to cell culture systems and more specifically to microfabricated, microfluidic culture systems for neurological research.

In accordance with an embodiment of the invention there is provided a microfluidic device comprising first and second compartments connected by micro-channels, each compartment consisting of a main chamber connected to first and second auxiliary rooms.

In accordance with an embodiment of the invention there is provided a method of manufacturing a microfluidic device comprising first and second compartments connected by micro-channels, each compartment consisting of a main chamber connected to first and second auxiliary rooms.

In accordance with an embodiment of the invention there is provided a method of culturing cells comprising: providing a microfluidic device comprising first and second compartments consisting of a main chamber connected to first and second auxiliary rooms with the main chambers connected by micro-channels, wherein
at least one each main chamber comprises a corner at each end of an end wall closest to an array of micro-channels along a sidewall of the main chamber, wherein the main chamber has at the other corners of the end walls the first and second auxiliary rooms and the corner has a high angle relative to the sidewall of the main chamber with micro-channels; and
at least one main chamber has a second sidewall substantially opposite a sidewall having micro-channels disposed along it, wherein the second sidewall has a profile selected from the group comprising a predetermined portion of at least one of an ellipse, a parabola, a hyperbola, a circle, and a predetermined mathematical function and the profile along the microfluidic device from its middle to the first auxiliary room reaches its closest to the other sidewall at a predetermined point between the first auxiliary room and the second auxiliary room; and
introducing the cells to be cultured into one of the first auxiliary room and the second auxiliary room.

In accordance with an embodiment of the invention there is provided a method of performing a medical test comprising:
providing a microfluidic device comprising first and second compartments consisting of a main chamber connected to first and second auxiliary rooms with the main chambers connected by micro-channels, wherein
at least one each main chamber comprises a corner at each end of an end wall closest to an array of micro-channels along a sidewall of the main chamber, wherein the main chamber has at the other corners of the end walls the first and second auxiliary rooms and the corner has a high angle relative to the sidewall of the main chamber with micro-channels; and
at least one main chamber has a second sidewall substantially opposite a sidewall having micro-channels disposed along it, wherein the second sidewall has a profile selected from the group comprising a predetermined portion of at least one of an ellipse, a parabola, a hyperbola, a circle, and a predetermined mathematical function and the profile along the microfluidic device from its middle to the first auxiliary room reaches its closest to the other sidewall at a predetermined point between the first auxiliary room and the second auxiliary room; and
introducing a biological specimen into one of the first auxiliary room and the second auxiliary room.

In accordance with an embodiment of the invention there is provided a microfluidic device comprising:
first and second compartments, each consisting of a main chamber connected to first and second auxiliary rooms;
a plurality of micro-channels interconnecting the pair of main chambers, wherein
at least one each main chamber comprises a corner at each end of an end wall closest to an array of micro-channels along a sidewall of the main chamber, wherein the main chamber has
at the other corners of the end walls the first and second auxiliary rooms and the corner has a high angle relative to the sidewall of the main chamber with micro-channels; and at least one main chamber has a second sidewall substantially opposite a sidewall having micro-channels disposed along it, wherein the second sidewall has a profile selected from the group comprising a predetermined portion of at least one of an ellipse, a parabola, a hyperbola, a circle, and a predetermined mathematical function and the profile along the micro-fluidic device from its middle to the first auxiliary room reaches its closest to the other sidewall at a predetermined point between the first auxiliary room and the second auxiliary room.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 17; depicts a cross-section third generation microfluidic device according to embodiments of the invention depicting various micro-channel geometries relative to the cells;

FIG. 18 depicts a third generation microfluidic device according to embodiments of the invention in perspective views, part assembled, and assembled;

DETAILED DESCRIPTION

Figure 1:
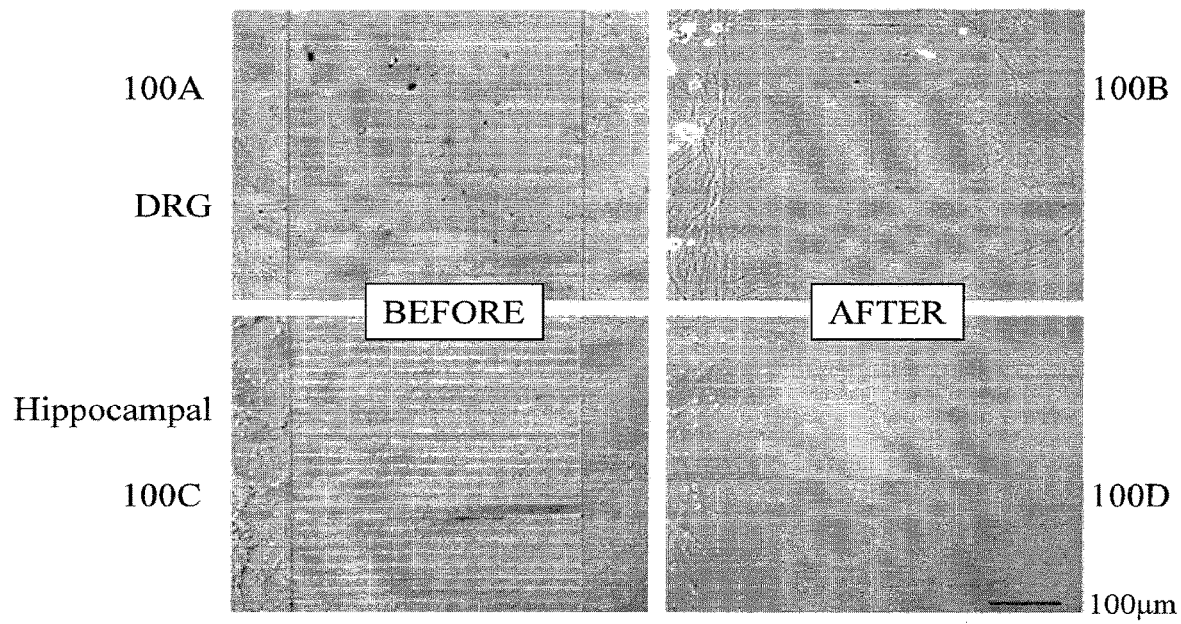
FIG. 1 depicts an in-vitro model to reproduce neuronal injury in the nanoscale together with optical microscopy images of dissociated rat DRG and hippocampal neurons prior to and after disassembly of the microfluidic chambers according to embodiments of the invention.
Figure 1:
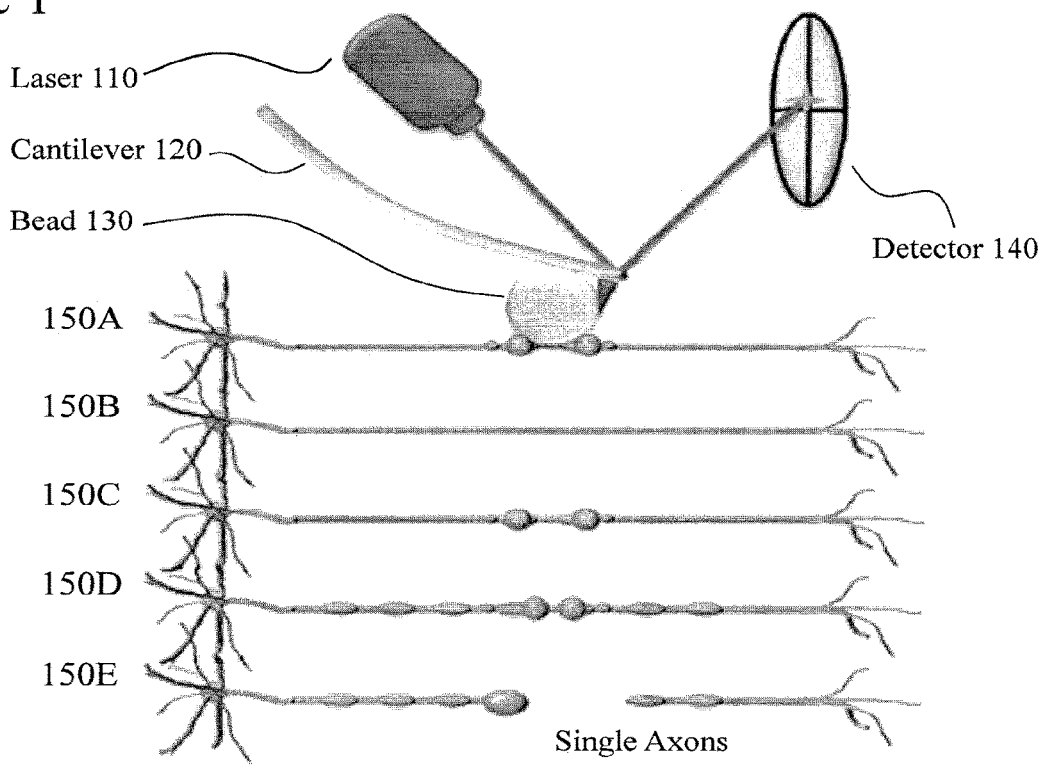

The present invention is directed to cell culture systems and more specifically to microfabricated, microfluidic culture systems for neurological research.

The ensuing description provides exemplary embodiment(s) only, and is not intended to limit the scope, applicability or configuration of the disclosure. Rather, the ensuing description of the exemplary embodiment(s) will provide those skilled in the art with an enabling description for implementing an exemplary embodiment. It being understood that various changes may be made in the function and arrangement of elements without departing from the spirit and scope as set forth in the appended claims.

A. Materials and Methods

A1: Microfluidic Chambers

Design and discussion of the microfluidic chambers according to embodiments of the invention are described and depicted in respect of FIGS. 7 and 10-18 in Part D.

The masters for the microfluidic chambers according to embodiments of the invention were manufactured in the McGill Nanotools Microfabrication Facility and prepared using polydimethylsiloxane (PDMS) using the Dow Corning™ Sylgard™ 184 silicone elastomer kit, see for example Park et al. in Reference [7]. The PDMS patterns were assembled onto 35-mm glass-bottom dishes or on 25-mm glass coverslips, coated with Poly-D-Lysine in order to promote the adhesion/attachment of cells.

A2: Neuronal Cultures

Hippocampal and DRG neurons from rat embryos of either sex were prepared, see References [8] and [9], and added to microfluidic chambers. The chambers were disassembled by removing the PDMS three and eight days after plating from DRG and hippocampal cultures, respectively. Without the physical PDMS barrier between channels, hippocampal and DRG axons move and extend neurites toward other axons, remodeling the culture architecture and losing the parallel pattern. In DRG cultures, these changes were much more accentuated and were apparent one day after PDMS removal, whereas in hippocampal axons contact between axons grown in different channels was only observed 3-4 days after PDMS removal. To minimize remodeling and maintain the parallel organization of the axons in the cultures, DRG neurons were cultured at a density four-times lower than hippocampal neurons and were tested within 7-10 days in culture, whereas hippocampal axons were tested after 14-18 days in culture. These changes in culture density and age did not result in significant differences in the axonal response to injury applied with this model. Where indicated, cells were treated with vinblastine sulfate salt ($C_{45}H_{58}N_4O_9$:$H_2SO_4$) diluted in neurobasal medium for 1 hour, washed and immediately tested with AFM or fixed with 4% paraformaldehyde for immunohistochemical analysis or Atomic Force Microscopy (AFM) imaging. Mitochondria were fluorescently labeled with MitoTracker™ Green FM and tubulin with Tubulin Tracker™.

A3: Immunocytochemistry

Immunocytochemistry was performed as described in Reference [8] with mouse anti-tubulin, rabbit anti neurofilament, rabbit polyclonal anti-Tom20 (mitochondrial preprotein translocases of the outer membrane FL-145); and Alexa Fluor™ 488 conjugated phalloidin. The secondary antibodies used were Rhodamine Red antimouse IgG and Alexa Fluor™ 647 anti-rabbit IgG. Samples were imaged using a laser scanning confocal microscope with a 60× PlanApo oilimmersion objective on an inverted microscope.

A4: Atomic Force Microscopy (AFM)

Simultaneous compression and live imaging of single axons were performed on a Bioscope AFM mounted on an inverted optical microscope using a 100× objective (1.45 NA) and 1 K charge-coupled device camera. Two different compression experiments were performed. In the first, a 20-mm polystyrene bead was fixed, see Reference [8], to the tip of silicon nitride probes with a nominal spring constant of k=0.01 N/m and used to compress axons with controlled force ranging from 0.1 nN≤F≤4 nN for different time periods. In the second, tipless n-type silicon probes with nominal spring constant of k=0.03 N/m were used to apply constant force to axons. Cells were mounted onto a heated stage and kept at 37° C. with constant $CO_2$ supply for the duration of the experiments. The AFM was used to localize and press the beaded or the tipless cantilever with sub-micrometer precision onto the top of the axons. Images of the culture were taken every 30 seconds for 5 to 10 minutes before compression to detect mitochondrial movement and axonal viability, during compression to detect any change in the axon that could indicate damage, and for 10 to 30 minutes after compression release to analyze axonal recovery. To model compression, a series of 15 force-distance curves in static mode were taken at 30 second intervals on each axon. During data acquisition, loading forces of 0.3 nN were employed.

AFM imaging was performed on fixed axons with two different instruments, yielding similar results. To achieve the best resolution and image the thinnest axons with the lowest forces, an Asylum Research MFP-3D-BIO AFM was mounted onto an Olympus inverted optical microscope, was used. Glass coverslips containing micro-patterned neurons in phosphate buffered saline (PBS) buffer were attached to a peak fluid cell using vacuum grease. A 60× oil immersion objective with NA=1.45 was placed underneath the sample allowing optical access from the bottom and topographical access from the top of the sample. The region of interest was located and aligned using a charge-coupled device camera. Silicon nitride micro-lever probes were used to image under liquid. The deflection inverse optical lever sensitivity was calibrated in air and buffer before experimentation following manufacturer protocols. The cantilever was oscillated at its first resonance frequency with an amplitude of ~0.6 nm. The deflection signal was low-pass-filtered and the resulting mean deflection signal was kept constant using a distance control feedback loop. The force applied to the sample throughout the scan was thus oscillatory and the average force (deflection) was set constant (~10 pN). Images were acquired at 0.25 Hz with 2562 points per line along a distance of 20 mm. Using this method, lateral force was reduced and the signal/noise ratio was increased. The spring constant of the cantilevers used was determined through theoretical calculations based on cantilever dimensions and material properties.

A5: Data Analysis

The Hertz model is the most commonly used model to determine the mechanical properties of cells, see References [10] to [12]. Using the Hertzian approximation, the inventors present an estimation of the elastic moduli of axons using nano-indentation with AFM. Given the geometry of our system, where axons were compressed between a bead attached to the cantilever tip and the glass, the elastic compression of a cylinder by a sphere and a plane was modeled considering Hertzian effects, see Reference [13]. The total compression is given by the total deformation, $\delta_{Total}$, which is related to the deformation of the cylinder (axon) by the bead, $\delta_{Bead-Cylinder}$, and the plane (glass) $\delta_{Plane-Cylinder}$, by Equation (1).

$$\delta_{Total} = \delta_{Bead-Cylinder} + \delta_{Plane-Cylinder} \quad (1)$$

Modeling the underlying glass plane as a sphere with an infinite radius, then the term accounting for the deformation induced by the plane is negligible. Using the method of Reference [13] the $\delta_{Bead-Cylinder}$ can be calculated using Equation (2) where $\gamma$ is the Poisson ratio of the axon or the bead, E is the Young's modulus of the material, F is the total force applied, e is the eccentricity of the ellipse of contact, and K and $$\frac{1}{e}\frac{dE}{de}$$

are the complete elliptic integrals of the first and second class, respectively, with modulus e. Accordingly, in physical concept, the force exerted by the bead is uniformly distributed along the contact plane. Therefore, the deformation, referred to here from as indentation, is mainly an effect of the bead compression as given by Equation (3).

$$\delta_{Bead-Cylinder} = \left(\frac{3}{2\pi}\right)^{\frac{2}{3}}\left[\left(\frac{1-\gamma^2_{Axon}}{E_{Axon}}\right)+\left(\frac{1-\gamma^2_{Bead}}{E_{Bead}}\right)\right]^{\frac{2}{3}} \times \left(\frac{K}{-\frac{1}{e}\frac{dE}{de}D_{Tip}}\right)F \quad (2)$$

$$F = \frac{\delta^{\frac{3}{2}}\left(\frac{2\pi}{3}\right)}{\left[\left(\frac{1-\gamma^2_{Axon}}{E_{Axon}}\right)+\left(\frac{1-\gamma^2_{Bead}}{E_{Bead}}\right)\right]\cdot\left(\frac{K}{-\frac{1}{e}\frac{dE}{de}D_{Tip}}\right)^{\frac{3}{2}}} \quad (3)$$

The indentation data were analyzed using least-squares regression and fitted with the modified Hertz model for spherical indenter as appropriate given in Equation (3). Statistical differences were assessed using Student's t-test for continuous data and were accepted as significant at $p<0.05$.

B: Experimental Results

In measuring the resistance of single DRG and hippocampal axons to compression and axonal resistance to compression, we performed nerve constriction experiments in the nanoscale by using microfluidic chambers to grow and linearly extend DRG and hippocampal axons in parallel channels separated from cell bodies and dendrites such as depicted in first to fourth images 100A to 100D respectively in FIG. 1, see Reference [46]. As depicted in first and third images 100A and 100C dissociated rat DRG and hippocampal neurons were grown in microfluidic chambers according to embodiments of the invention. Neurons were added to the somatodendritic-side of the chambers and their axons extended into the axonal chamber through microgrooves. After 3-8 days in culture, the microfluidic chambers according to embodiments of the invention were disassembled by removing the PDMS from the coverslip without damaging the cells. These are depicted in second and fourth images 100B and 100D respectively. The DRG and hippocampal neurons were kept in culture for 7 and 14 days, respectively, before the axons were tested with the AFM. Within the AFM testing the DRG and hippocampal axons grown in parallel channels were gradually compressed with sub-nanoNewton (nN) forces applied by a bead 130 attached to the tip of the AFM cantilever 120 wherein the deflection of cantilever 120 was measured using optical means through reflection of a laser 110 output onto a position sensitive detector 140. The axonal response to compression depended upon the time and force applied of the tip 130 yielding compressed axon 150A. Four distinct responses were identified after compression release, these being:

axons recovered their original state, as depicted in normal axon 150B;
  axons stayed permanently deformed, as depicted in deformed axon 150C;
  degenerative process with increasing formation of FAS, as depicted in FAS axon 150D; and
  rupture of the axon; as depicted in ruptured axon 150E.

The microfluidic chamber consists of a polydimethylsiloxane (PDMS) mold with a pattern of somatodendritic and axonal compartments connected by microgrooves adhered to a Poly-D-Lysine coated coverslip. The Poly-D-Lysine coating being as per Reference [7]. To mimic nerve constriction, the inventors removed the PDMS and used the AFM to compress the axons grown in the microchannels. To follow axonal transport and viability, the inventors fluorescently labeled mitochondria and imaged the axonal response to compression. The use of microfluidic chambers significantly facilitated the control and reproducibility of the data.

Because the axons grow in parallel within microfluidic chambers according to embodiments of the invention, the compression may be applied at approximately the same distance from the soma on each axon, ~200 μm from the cell body chamber. Further, as the single axons or bundles, according to the parameters of the micro-channels within the microfluidic chambers according to embodiments of the invention, grew in individual channels typically 50 μm apart from each other, improved precision in the placement and access of the AFM cantilever tip to the target axon(s) could be achieved. Controlled compression was performed as depicted in FIG. 1 with a bead 130 approximately 20 times larger than the axonal diameter, the bead 130 being attached to the tip of the AFM cantilever 120, see also Reference [8]. Usage of a bead 130 guaranteed that the observed axonal damage and response were due to compression forces of the bead 130 and not due to piercing or damaging of the axonal membrane with the sharp tip of the AFM cantilever 120. The bead 130 distributes the pressure along the axonal diameter thereby mimicking physiological nerve compression conditions. Experiments were performed compressing the axons with applied forces ranging from $0 \text{ nN} \leq F \leq 7.5 \text{ nN}$.

Topographic AFM images from the axons also allowed the evaluation of the axonal height, width, and indentation of the AFM cantilever 120 according to the applied force. The average width of DRG axons and hippocampal axons tested were not significantly different (respectively, 1068±429 nm and 1019±476 nm). This data was used to estimate the area of contact between the bead and the axons and to calculate the applied pressure. The inventors found a direct relationship between compression forces and axonal injury. Compression with 550±220 Pa led to the progressive collapse of hippocampal growth cones and reduction of mitochondrial signal and movement followed by axonal rupture, formation of retraction bulbs and neuronal degeneration as depicted in FIG. 2. The axonal response to compression was the same when pressure was applied close to or distant from growth cones. By decreasing the pressure to 320±150 Pa, focal axonal swelling (FAS) formed along the whole axon and remained even after pressure release, suggesting blockade of axonal transport also in regions distant from the compression point.

Figure 2A:
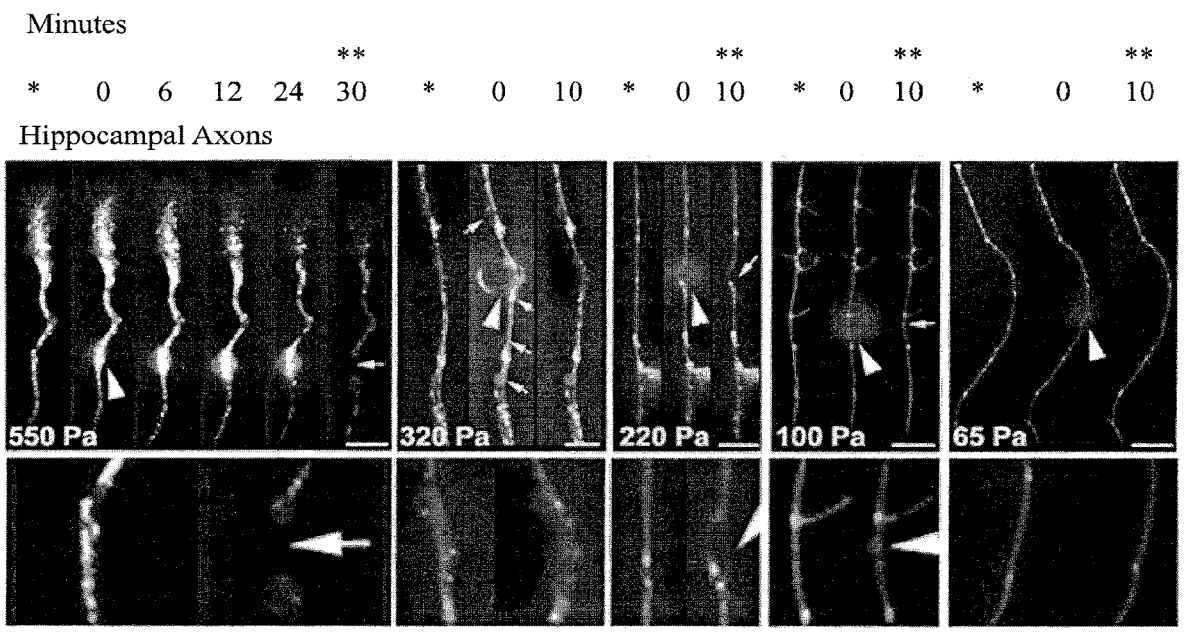
FIG. 2A to 2D depicts DRG axon measurements performed using axons grown and cultured within microfluidic chambers according to embodiments of the invention.

Compression between 200±90 Pa and 130±60 Pa resulted in local deformation of the axon under the compression point, which persisted after compression release as evident from FIG. 2A wherein residual local deformation is marked by arrows. Depicted within FIG. 2A each image has been orientated such that the cell soma lies below the axonal segment shown in the panels wherein the white scale bar is 10 μm. The images in FIG. 2A were obtained, see Reference [46], with mitochondria that were fluorescently labeled and single axons that were compressed with a bead tipped AFM cantilever described supra in respect of FIG. 1 with pressures ranging from $65 \text{ Pa} \leq P \leq 50 \text{ Pa}$ for 10 to 30 minutes. Images taken before (*), during, and after compression (**) show that hippocampal axons do not recover axonal shape and mitochondria transport after compression release when compressed with pressures P>65 Pa for 10 minutes, the lower panels within FIG. 2A which are 3× zoom images of the compression regions of the axons before compression and after compression release within the upper panels. Each panel represents one axon but at least 10 axons were tested in each condition with similar results. All hippocampal axons tested only recovered their shape and mitochondrial movement if compressed with P=65±30 Pa or less for 10 minutes. However, as evident from FIG. 2D wherein the percentage of irreversibly damaged axons versus applied pressure is depicted, when hippocampal axons were compressed with P=100±50 Pa only 40% of the axons tested recovered. Each bar represents the result of at least five axons tested under the same conditions.

Figure 2B:
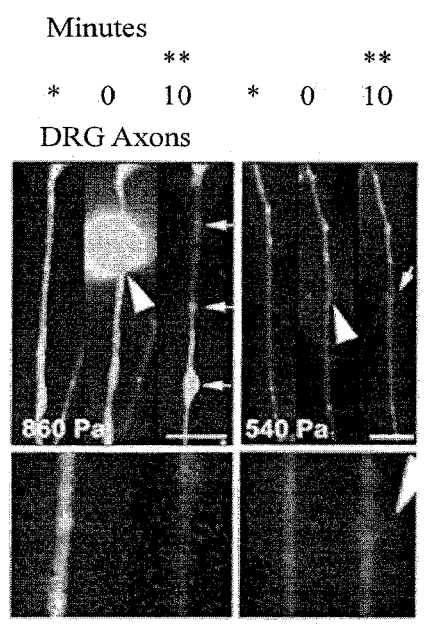
Figure 2C:
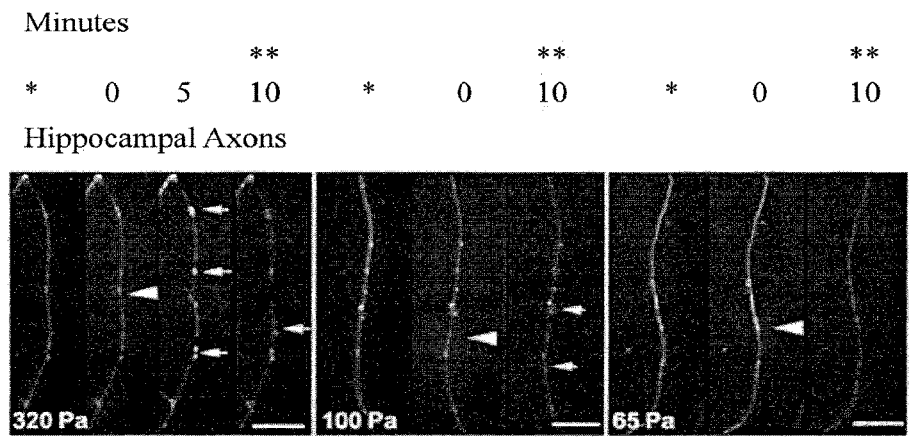
Figure 2D:
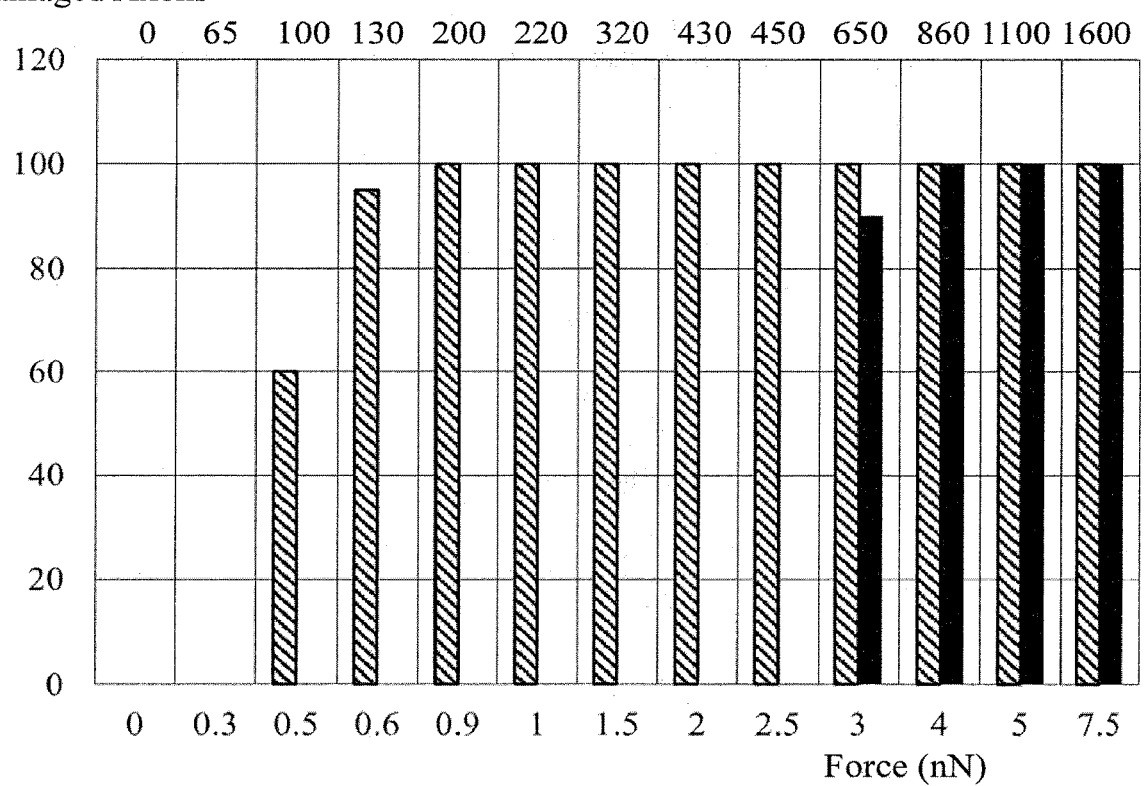

The inventors also tested DRG axons and found that these pressures up to P=540±220 Pa for 10 minutes and damaged axons were observed only with pressures in the range of P=860±350 Pa or higher as depicted in FIG. 2B, see Reference [46]. These data indicate a significant difference between the mechanical, resistance of hippocampal and DRG axons. Next, the inventors investigated the effects of compression on the axonal cytoskeleton. For this the inventors labeled axonal tubulin and compressed axons with different forces observing that compression of hippocampal axons with pressures P<100±50 Pa for 10 minutes causes a local blockade of axonal transport whereas higher pressures lead to multifocal blockade of axonal transport, with accumulation of tubulin and mitochondria in FAS distant from the compression point and distributed along the whole axon. Referring to FIG. 2C, see Reference [46], the same compression experiment as described in respect of FIG. 2A was performed with hippocampal axons fluorescently labeled with Tubulin Tracker™, revealing the formation of FAS containing tubulin when the pressure exceeds P>65 Pa. Each panel represents one axon but at least eight axons were tested in each condition with similar results. The axons that recovered after compression injury only show FAS close to the compression point whereas all axons presenting with multiple FAS spots did not recover after compression release.

Figure 3A:
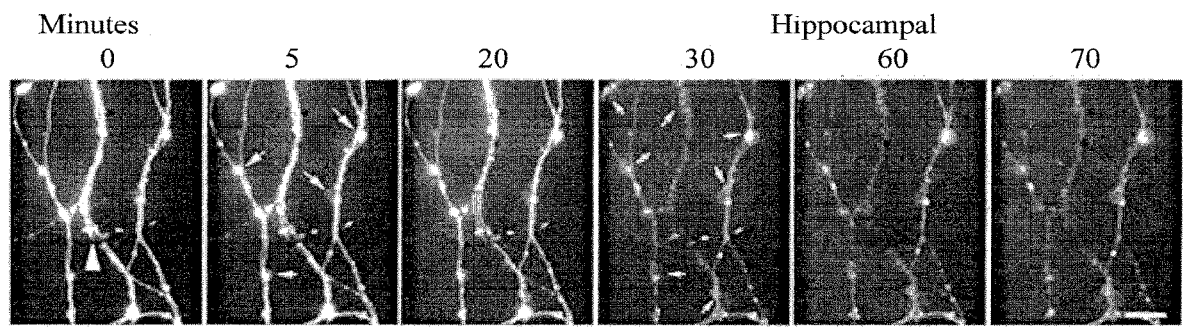
FIGS. 3A to 3D depict the progressive formation of focal axonal swelling during axonal compression FIG. 3 and the corresponding volumetric changes for hippocampal and DRG axons respectively.
Figure 3B:
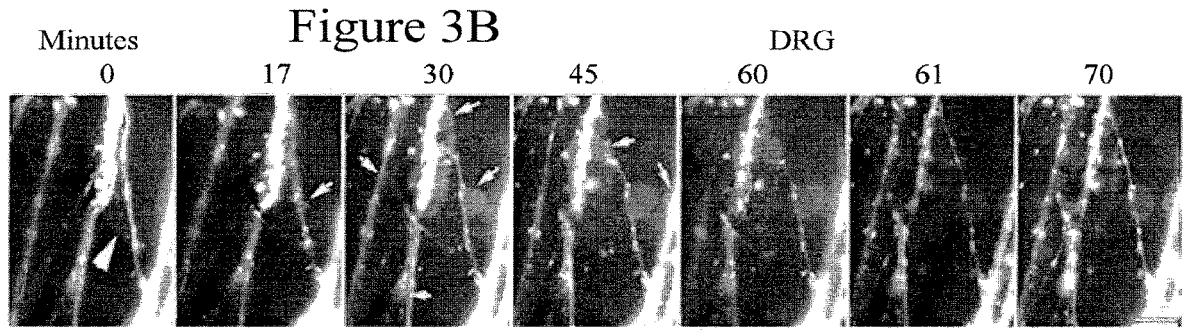

It was evident that both hippocampal and DRG axons undergo different morphological changes due to impairment of axonal transport The most characteristic morphological change that we observed during axonal compression was the formation of focal axonal swelling (FAS). To better evaluate the formation of FAS close to the compression point on axons the inventors changed the AFM cantilever to a tipless cantilever, which enabled us to apply compression to more than one axon at the same time yielding the results depicted in FIGS. 3A to 3D respectively, see Reference [46]. Referring to FIG. 3A mitochondria were fluorescently labeled and hippocampal axons were compressed for 60 minutes with 540±220 Pa with the tipless AFM cantilever. In FIG. 3B DRG axons were compressed with 1100±440 Pa in the same conditions as in FIG. 3A. In each the discrete arrowheads depict the compression site whereas newly appearing FAS or increases in FAS size during compression are depicted as arrows. In each instance the soma lies below the axonal segment shown in the panels. The scale bar in each of FIGS. 3A and 3B respectively is 10 μm.

Figure 3C:
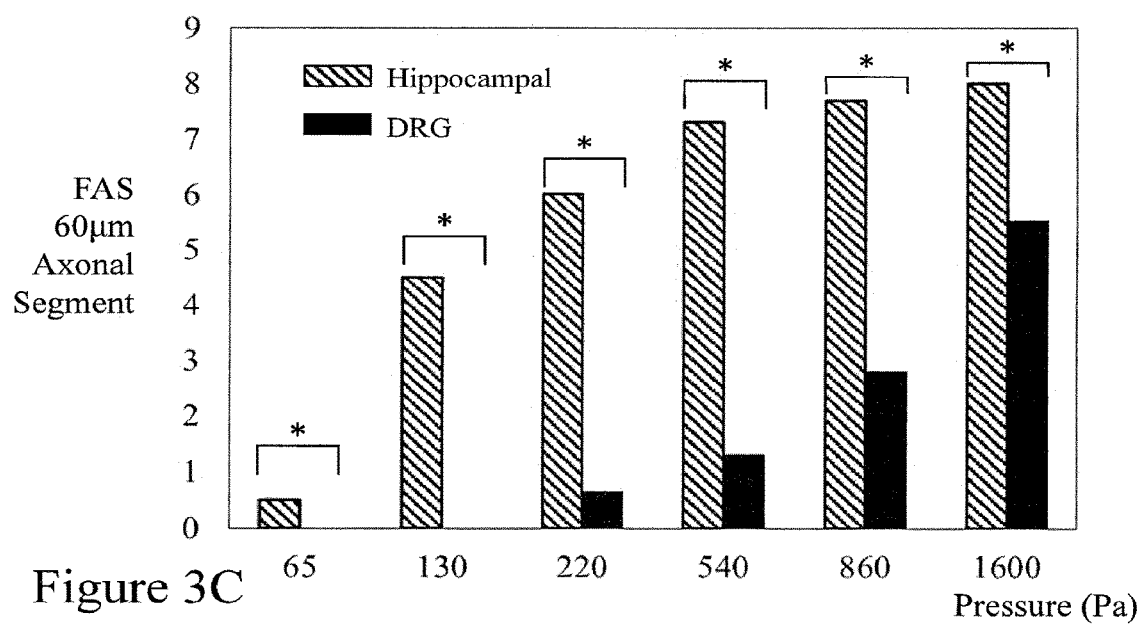
Figures 3D, 4C:
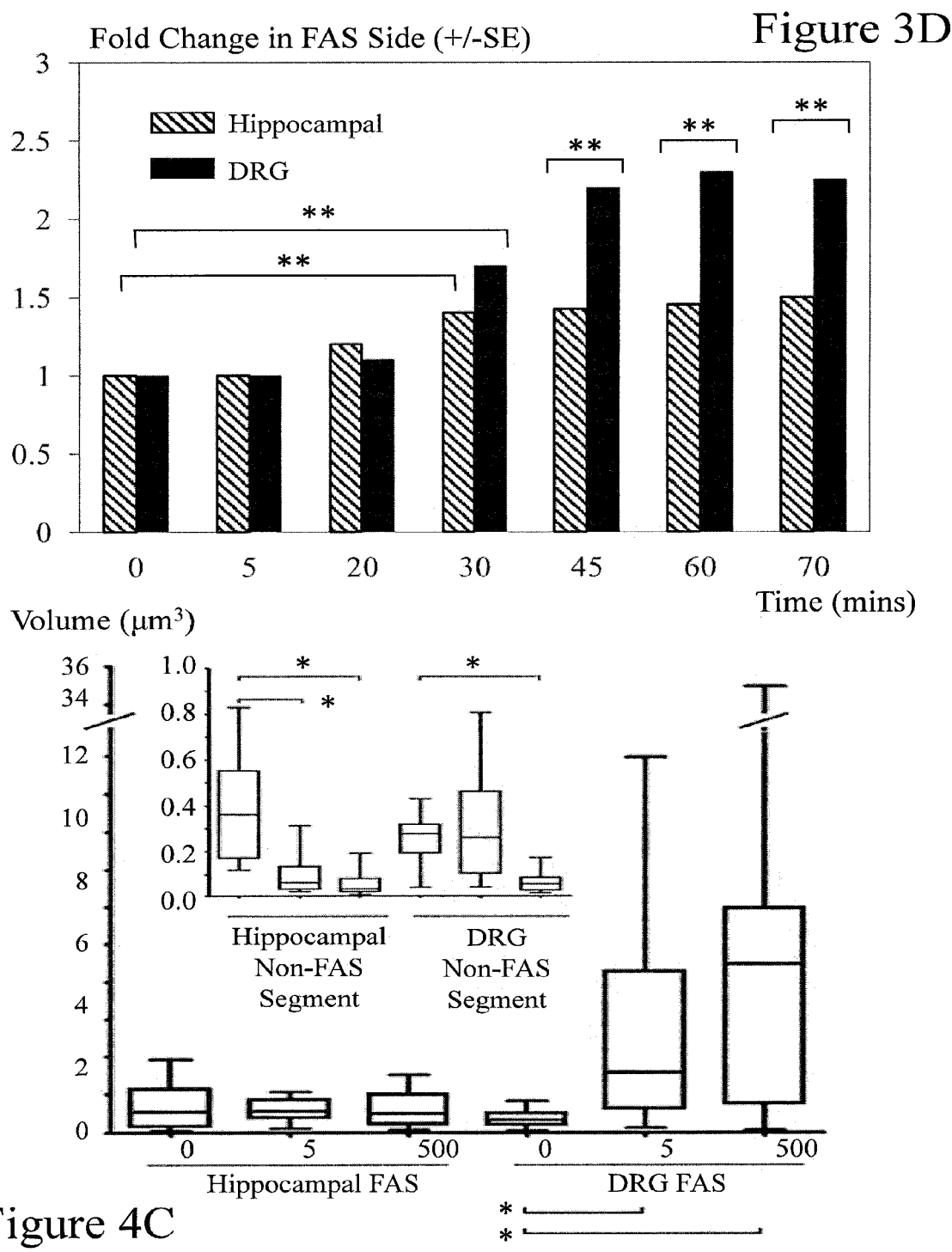
FIGS. 4A to 4C depict the progressive formation of FAS during gradual impairment of axonal transport arising from chemically induced damage.

Referring to FIG. 3C there is depicted a plot showing the average number mean of FAS formed in each 60 μm axonal segment (n=14) after compression of hippocampal and DRG axons for 10 minutes with different pressures (*$p<0.001$). FIG. 3D depicts the increase in the size of FAS during compression of hippocampal and DRG axons for 60 minutes with 540 Pa and 1500 Pa, respectively. The increase in FAS area was determined by setting a region of interest corresponding to each FAS at the end of compression, then using the National Institutes of Health software Image J, see Reference [44] to measure the fluorescent area in each region of interest over the images acquired at different time points, thereby enabling the calculation of the increase in the area of FAS during compression. Each bar corresponds to the average increase in the area of at least 20 FAS during compression (**$p<0.05$).

Local increases of axonal width 10% or in axonal height, 20%, were considered as FAS. Accordingly, the inventors found that ~30% of hippocampal and DRG axons presented 1-3 small FAS before any treatment. As compression was applied, the number and size of FAS increased with the increase in compression time and force being applied as evident from FIGS. 3A and 3B. Hippocampal axons formed more but smaller FAS than DRG axons as evident in FIGS. 3C and 3D. In both types of axons, compressions with lower forces induce the formation of one or two FAS close to the compression point, which usually disappeared after compression release. However, when three or more FAS were formed along the axons, the axons did not recover their shape after compression release. The progressive formation of FAS in response to axonal injury highlights the importance of the development of early FAS markers for the application of potential therapeutic interventions, especially after brain trauma, as the number and size of FAS in the brain of injured patients is directly related to the degree of axonal damage and neuronal loss, see Reference [4]. In healthy axons, axonal transport flows on microtubules and focal blockade of axonal transport and loss of microtubules leads to the accumulation of transported material and formation of FAS, se References [2] and [14] to [16]. Blockade of axonal transport can be achieved by compression, as we showed above, or by disruption of microtubules. To further characterize the formation of FAS during axonal injury we treated axons with increasing concentrations of vinblastine, which prevents polymerization of tubulin and induces depolymerisation of formed tubules, see Reference [17].

Subsequently, the inventors characterized the axonal morphological changes in three dimensions using AFM. Axons treated with vinblastine sulphate salt showed the same morphological features as axons compressed with high pressure in that they formed multiple FAS along their length as evident from FIGS. 4A to 4C and that the number and size of FAS increased with increasing vinblastine concentrations. This axonal injury had a strong resemblance to the one caused by the increase in compression time and force and resulted in a proportional degree of interruption in axonal transport, evident from comparing FIGS. 3A and 3B to FIGS. 4A and 4B. Further, in agreement with the compression data in FIGS. 3A to 3C the shape and size of FAS in the DRG axons was different from that observed in hippocampal axons in that the FAS in DRG axons, lower panels in FIG. 4A, was significantly larger than those of hippocampal axons, upper panels in FIG. 4B.

Figure 4A:
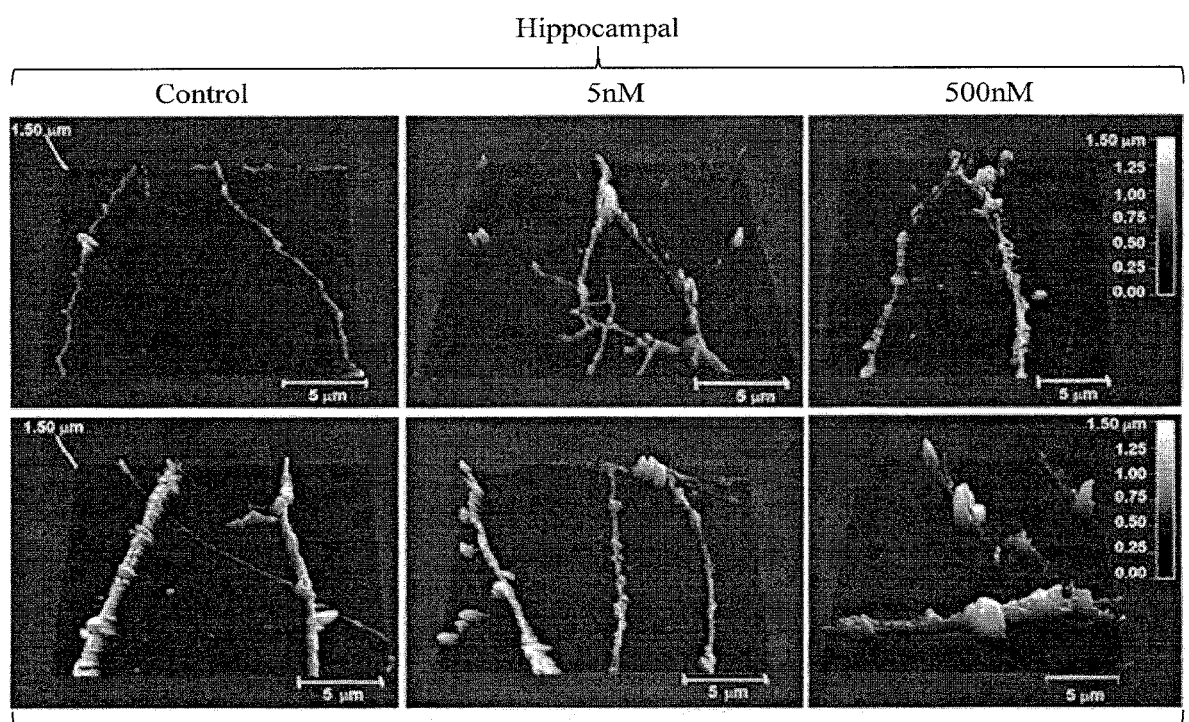
Figure 4B:
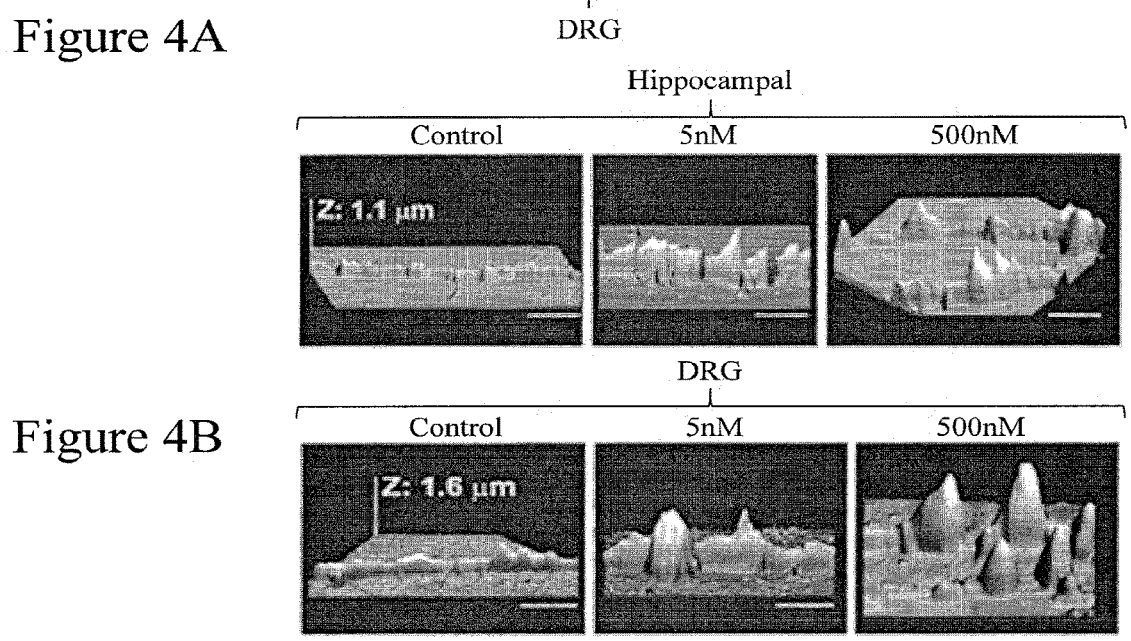

In FIGS. 4A and 4B DRG and hippocampal axons were observed for progressive formation of FAS during gradual impairment of axonal transport through visualizing control axons against those treated with 5 nM or 500 nM vinblastine for 1 hour after which they were fixed and imaged with the AFM, see Reference [46]. The images in FIG. 4B were made by focusing onto the FAS wherein the scale marker is 5 μm. Then referring to FIG. 4C so called box-and-whiskers plots showing the minimum and maximal volume of each FAS formed by hippocampal and DRG axons treated with increasing concentrations of vinblastine were generated. The insert in FIG. 4C depicts the minimum and maximal volume of an axonal segment between FAS (*$p<0.0001$). At least 23 axons were imaged and measured for each experimental condition. Accordingly, it is evident from FIG. 4C that the increasing disruption of axonal transport with increasing vinblastine concentrations had different effects on the morphology of DRG and hippocampal axons. The volume of single FAS in DRG axons increased with increasing vinblastine concentrations whereas the volume of single FAS in hippocampal axons did not significantly change suggesting that DRG axons are more elastic than hippocampal axons and can accommodate a remarkably large local increase in diameter at FAS. The inventor also noted, insert in FIG. 4C, that the volume of axons in regions between FAS, so-called non-FAS segments, reduced with increasing vinblastine concentrations and that the hippocampal and DRG axons had collapsed. In hippocampal axons, the volume of the non-FAS segment decreased at 5 nM vinblastine and in DRG axons at 500 nM vinblastine.

To investigate the reason for the higher resistance of DRG axons to compression and to vinblastine effects, the inventors investigated the composition and distribution of cytosolic components in axons with impaired transport. The composition of the axonal cytoskeleton is critical to determine the axonal elasticity and, consequently, the degree of axonal susceptibility to damage. We analyzed the distribution of mitochondria, actin, neurofilament, and tubulin after blockade of axonal transport. During compression of DRG and hippocampal axons the inventors observed loss of mitochondrial labeling and mitochondria accumulation in FAS, see FIGS. 2A and 2B and FIGS. 3A and 3B. Similarly, in vinblastine-treated axons, the distribution of mitochondria changed from uniform to a discontinuous punctate pattern, co-localizing with tubulin at FAS. In axons treated with vinblastine, actin too FAS close to the compression point usually disappeared after compression release. However, when three or more FAS were formed along the axons, the axons did not recover their shape after compression release. The progressive formation of FAS in response to axonal injury highlights the importance of the development of early FAS markers for the application of potential therapeutic interventions, especially after brain trauma, as the number and size of FAS in the brain of injured patients is directly related to the degree of axonal damage and neuronal loss, see Reference [4]. In healthy axons, axonal transport flows on microtubules and focal blockade of axonal transport and loss of microtubules leads to the accumulation of transported material and formation of FAS, see References [2] and [14] to [16]. Blockade of axonal transport can be achieved by compression, as we showed above, or by disruption of microtubules. To further characterize the formation of FAS during axonal injury we treated axons with increasing concentrations of vinblastine, which prevents polymerization of tubulin and induces depolymerisation of formed tubules, see Reference [17].

Next, the inventors characterized the axonal morphological changes in three dimensions using AFM. Axons treated with vinblastine showed the same morphological features as axons compressed with high pressure. They formed multiple FAS along their length as evident from FIGS. 4A to 4C with the number and size of FAS increasing with increasing vinblastine concentrations. This axonal injury had a strong resemblance to the one caused by the increase in compression time and force and resulted in a proportional degree of interruption in axonal transport, comprising FIGS. 3A and 3B to FIGS. 4A and 4B. In agreement with the compression data the shape and size of FAS in DRG axons were different from those in hippocampal axons, with FAS in DRG axons being remarkably larger than those of hippocampal axons. The effects of multifocal blockade of axonal transport on the whole axonal cytoarchitecture was investigated by the inventors estimating the volume of FAS in at least three segments along each axonal filament, see FIG. 4C. The inventors found that the increasing disruption of axonal transport with increasing vinblastine concentrations had different effects on the morphology of DRG and hippocampal axons. The volume of single FAS in DRG axons increased with increasing vinblastine concentrations whereas the volume of single FAS in hippocampal axons did not significantly change suggesting that DRG axons are more elastic than hippocampal axons and can accommodate a remarkably large local increase in diameter at FAS. The inventors also evaluated the volume of axons in regions between FAS (non-FAS segment). With increasing vinblastine concentrations, hippocampal and DRG axons collapsed. In hippocampal axons, the volume of the non-FAS segment decreased at 5 nM vinblastine and in DRG axons at 500 nM vinblastine, FIG. 4C insert.

To investigate the reason for the higher resistance of DRG axons to compression and to vinblastine effects, the inventors investigated the composition and distribution of cytosolic components in axons with impaired transport. The composition of the axonal cytoskeleton is critical to determine the axonal elasticity and, consequently, the degree of axonal susceptibility to damage. The inventors analyzed the distribution of mitochondria, actin, neurofilament, and tubulin after blockade of axonal transport. During compression of DRG and hippocampal axons, the inventors observed loss of mitochondrial labeling and mitochondria accumulation. Similarly, in vinblastine-treated axons, the distribution of mitochondria changed from uniform to a discontinuous punctate pattern, co-localizing with tubulin at FAS. In axons treated with vinblastine, actin concentrated between FAS and when it co-localized with FAS, actin formed cuplike structures apparently around FAS. Neurofilaments and microtubules collapsed and accumulated at FAS. With increasing vinblastine concentration, there was a proportional increase in tubulin and neurofilament aggregation at FAS. The observed collapse of neurofilaments is likely due to neurofilament destabilization subsequent to microtubule collapse, because microtubules interact with neurofilaments, see References [18] and [19], and vinblastine does not directly cause neurofilament disassembly, see Reference [20]. These data indicate that the composition of FAS is very similar in DRG and hippocampal axons and includes mitochondria and fragments of tubulin and neurofilaments, but not F-actin. It is possible that vesicles and other cellular components transported along axons might also accumulate in FAS.

After vinblastine treatment, DRG axons appeared to have more and larger FAS. This pattern coincides with previous data obtained from compressed DRG axons, which formed larger FAS than hippocampal axons. Given that the DRG and hippocampal axons tested had very similar caliber, larger FAS indicates that DRG axons may have a larger flow of transported material or higher content of tubulin or neurofilament. Because the structure of DRG axons after vinblastine treatment was more stable, see FIGS. 4A to 4C respectively, the inventors decided to compare the amount of actin, tubulin, and neurofilament in DRG and hippocampal axons. The inventors found that DRG axons contain approximately seven times more neurofilament than hippocampal axons whereas actin and tubulin amounts are very similar in both axonal types. This is similar to previous results demonstrating that neurofilament/tubulin ratios are nearly threefold greater in PNS (axons from the sciatic nerve) than in CNS (axons from the optic nerve) axons, see Reference [21]. These differences in cytoskeleton composition are likely reflected in the axonal viscoelastic properties and resistance to injury. The composition of the axonal cytoskeleton is critical to determine the axonal elasticity and the degree of axonal susceptibility to damage because each component of the axonal cytoskeleton has different elastic properties. Neurofilaments are more flexible than actin, softer than microtubules, and can withstand large strains, providing cells with pliancy to accommodate small deformations while strengthening them when large stresses are applied. See Reference [22].

Figure 5A:
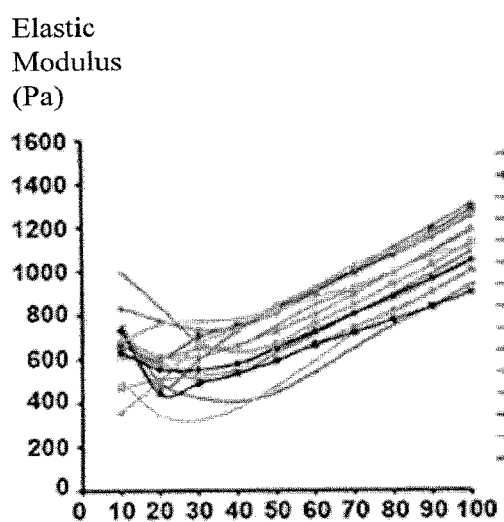
FIGS. 5A to 5B depict the elasticity of DRG and hippocampal axons.
Figure 5B:
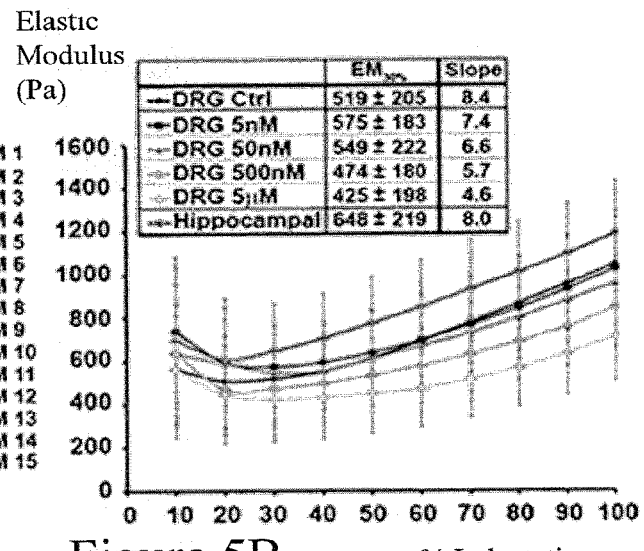
Figure 5C:
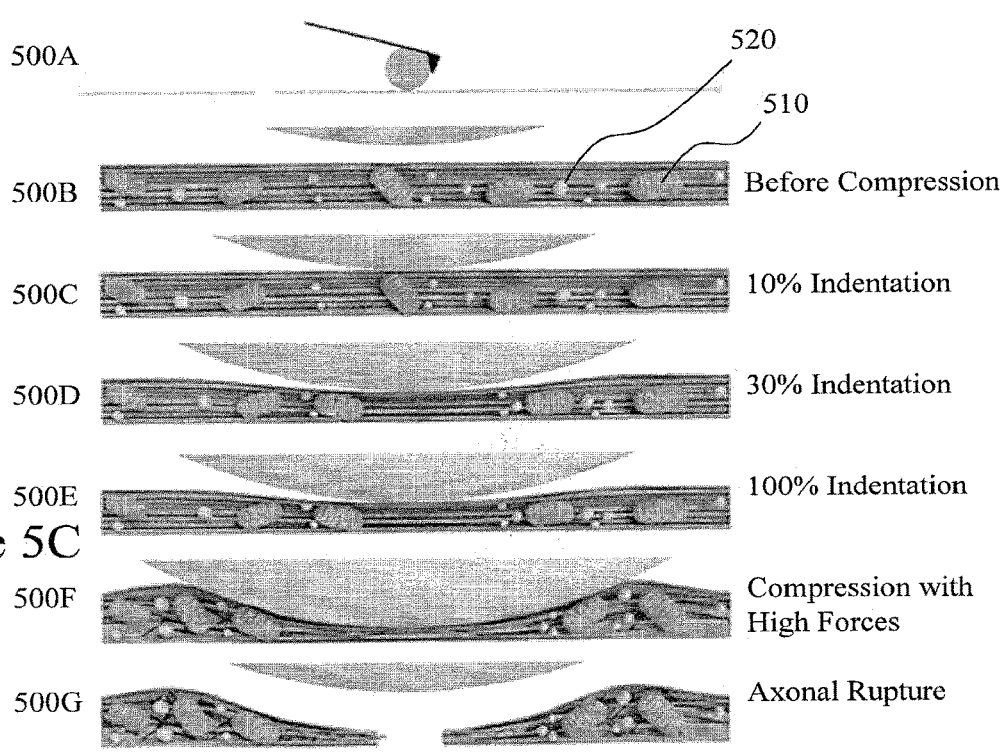
FIG. 5C depicts a model of axon compression under a 20-mm bead attached to the AFM cantilever.

Measuring the elasticity of individual axons was subsequently performed. Referring to FIG. 5A, see Reference [46], there are depicted plots for the estimated elastic modulus as function of percentage indentation of 15, denoted as EM 1-15, force-distance curves performed on one DRG axon at intervals of 30 second each, showing the high elastic modulus variability in the first 10-20% of indentation. The maximum (100%) indentation of the cantilever corresponds to approximately half of the axonal height. Referring to FIG. 5B there are depicted the average elastic modulus and standard deviation of at least 10 hippocampal and 10 DRG axons treated or not with vinblastine (5 nM-5 µM). In order to compare the elastic modulus of different axons treated under different conditions, the inventors considered the average elastic modulus at 30% of indentation (EM30%), when the value is very similar to the elastic modulus at 10-40% but presented lower variation. Moreover, at 30% indentation the axonal stiffening as a function of compression is not as evident as at 50% or higher indentations. As evident from the insert table in FIG. 5B increasing vinblastine concentrations decreased the average EM30% and the slope of the curve. Referring to FIG. 5C the inventors depict graphically a model to scale of a 0.6 mm×1.0 mm axon being compressed by a 20 mm bead attached to the AFM cantilever, first image 500A. In second to seventh images 500B to 500G the effect if increasing compression on the axon is depicted showing the mitochondria 510, vesicles 520, tubulin and actin within the lower axon structure and neurofilament in the upper axon structure.

Accordingly, the measurements depicted in FIGS. 5A and 5B allow the determination of whether the differential susceptibility of hippocampal and DRG axons to mechanical injury is indeed influenced by differences in elasticity due to differing cytoskeletal architecture. Elastic modulus quantifies the tendency of a material to be non-permanently (elastically) deformed when a force is applied to it, with a stiffer material having a higher elastic modulus. The inventors calculated the axonal elastic modulus using the Hertz contact model with modifications to accommodate the geometry of the sample, considering the axon as a cylinder compressed by a sphere. The inventors found that the elastic modulus of DRG axons was approximately 20% lower than that of hippocampal axons at every indentation depth ($p<10^{-5}$). The average elastic modulus variation strongly correlated with the depth of cantilever indentation and the elastic modulus constantly increased after 30% indentation in all axons tested, see FIGS. 5A and 5B. Depth-dependent increases in the elastic modulus of biological samples have been reported by different groups suggesting that cell stiffness increases as compression increases, but the reasons for this effect have not been clarified, see Reference [10]. In general, the response of cells to applied force can be divided into two parts, the first, a mechanical response, see References [23] to [25], consisting simply of the deformation of the cell's loadbearing structures, and the second, a biochemical signaling response, which potentially leads to most force-induced phenotypic changes, see References [26] to [28]. However, it is not yet understood in detail how strain, i.e. force, propagates through different intracellular structures, see Reference [29].

The intracellular environment is probably very dynamic in accommodating the compression forces, triggering different pathways and modifying the cytosolic architecture to avoid major damages. Therefore, understanding the origins of axonal stiffness is of fundamental importance to prevent axonal damage and consequent neuronal dysfunction. To test whether the depth-dependent increase in axonal stiffness was caused by substrate or cytoskeleton resistance, the inventors evaluated the elastic modulus of vinblastine-treated axons. The slope of the elastic modulus curve as a function of percentage indentation decreased proportionally with increasing vinblastine concentration, see FIG. 5B, confirming that cytoskeleton resistance is responsible for the depth-dependent increase in axonal stiffness. Treatment with 5 nM vinblastine significantly decreased the EM30% ($p<0.001$) and the remaining slope in the elastic modulus curve of axons treated with 5 nM vinblastine is probably due to the stiffness of actin filaments that remain after vinblastine treatment.

The inventor's hypothesis for the occurrence of differential axonal resistance to injury is that different axonal components play a major role in the mechanical resistance of axons, depending on the deformation of the axon (indentation depth) and on the component capacity to accommodate stress. This hypothesis is reinforced by our data indicating that the depth-dependent increase in the axonal elastic modulus is inversely proportional to the integrity of the cytoskeleton, see FIGS. 5A and 5B. The inventors propose that the high variation in elastic modulus observed at 10% indentation is caused by the AFM sensing axonal transport under the tip because at 10% indentation the axonal lumen is not sufficiently reduced to impair axonal transport, see third image 500C. At moderate compression, e.g. 30%, the axonal lumen is reduced and mitochondria and larger vesicles start to accumulate, and the AFM tip then senses the resistance of the axonal cytoskeleton in addition to some axonal transport, fourth image 500D. As the compression deepens further, axonal transport becomes increasingly blocked, the variability of the axonal elastic modulus decreases, see FIG. 5A, and the axonal response to compression becomes more homogeneous, suggesting that the cantilever is compressing the axonal cytoskeleton, see fifth image 500E. Cytoskeleton resistance to compression is limited and, when hippocampal or DRG axons are compressed with larger forces (0.3 nN or 4 nN, respectively) for more than 10 minutes, irreversible changes take place and the cytoskeleton collapses, see sixth image 500F. Axonal transport is not restored after compression release and the axon is divided into two segments, see seventh image 500G. This suggests that the factor determining whether an axon will be severed or recover after damage is the elasticity and integrity of the cytoskeleton.

C: Discussion

The mechanism of axonal degeneration is quite similar in traumatic injuries and in chronic neurodegenerative diseases. The proposed model for axonal loss is that nerve insults lead to interruption of axonal transport, formation of FAS, increase in intra-axonal calcium levels, mitochondria dysfunction, and calcium-dependent cytoskeletal breakdown (for recent reviews, see Reference [2] and Reference [30]. Shortly after axonal injury, calcium influx has been shown to induce activation of proteases and the opening of the mitochondrial membrane permeability transition pore, resulting in pathologic swelling, loss of function, and local energy failure, see References [1], [2], [31], and [32]. Primary microtubules damage has also been shown to occur minutes after trauma, see References [2], [6], [16], and [33]. Together, these events are thought to represent the terminal events leading to axonal disconnection and degeneration. Axons are continually subjected to mechanical stimulation by external and internal forces but, when the forces exceed a certain threshold, the result is irreversible injury and axonal degeneration. Quantifying the forces is a first step in understanding the sequence of events that ultimately lead to the different stages of neuronal injury. Several groups have studied the pressure threshold for injury of CNS and PNS axons.

However, absent axonal samples and more specifically single axonal samples achievable through axonal/neuron growth using microfluidic structures according to embodiments of the invention have been hindered (limited) and have been made without the interference of the surrounding nerve environment. Indeed, the pressure threshold for axonal injury of PNS nerves was estimated at 30 mmHg (4 kPa) but compression with 20 mmHg (2.7 kPa) was shown to decrease blood flow inside PNS nerves and pressures of 30 mmHg (4 kPa) were described to impair axonal transport and cause a persistent increase in the pressure inside the nerve, edema, and nerve demyelination, see References [34] to [37]. In the CNS, the cornerstones of intensive care units include monitoring and management of patients' intracranial pressure (normally between $0 \leq P \leq 1.3$ kPa) and therapy aiming at reducing intracranial pressure when it exceeds $P \geq 2.0$-2.7 kPa, see Reference [38]. These limits are higher than the ones the inventors have found because they evaluate the consequences of pressure in the whole tissue whereas the inventor's studies have been focused specifically to the single axonal response through the exploitation of microfluidic devices for sample growth and sample presentation as evident from the descriptions below in respect of embodiments of the invention. Within the literature prior to the inventor's research there was no other study evaluating the response of single axons to injury caused by local compression with forces on the sub-nanoNewton scale with which the inventors could compare our values. In addition, there is no model available to evaluate how the global intracranial pressure measured within hospital, emergency, and field environments translates into local pressures on the different brain micro-environments and how elevated intracranial pressure might directly affect single axons. Interstitial fluid surrounding axons may act as a shock absorber or enhancer, and different situations such as trauma, edema, vascularization problems, brain tumors, stroke, infections, neurodegenerative diseases, or even surgery can significantly cause local increases in axonal pressure that may lead to degeneration. Dynamic deformation of axons rarely leads to primary disconnection during brain trauma, see References [1], [4], and [39]. Instead, disconnection occurs throughout the brain after focal axonal changes related to focal impairment of axonal transport, such as the FAS that the inventors observed in FIGS. 3A to 5C respectively. Accordingly, in the experimental results presented supra in respect of FIGS. 1 to 5C the inventors have exploited atomic force microscopy as both mechanical tool and imaging instrument to locally compress DRG and hippocampal axons. The inventors have been able to demonstrate using microfluidic device according to embodiments of the invention that isolated discrete DRG axons are more resistant to compression and more elastic than isolated discrete hippocampal axons. The inventor's propose that differences in the cytoskeletal composition are reflected in the viscoelastic properties of axons and accordingly play a significant role in axonal resistance to damage.

Notably, the proportions and architecture of the main components of the axonal cytoskeleton change during development and myelination, see Reference [40]. Demyelination, a common event in different degenerative diseases (in the CNS such as multiple sclerosis or Leukodystrophies and in the PNS such as Guillain-Barre' syndrome or Charcot-Marie-Tooth Disease), has been shown to increase neurofilament density, decrease microtubules density, and slow axonal transport in the PNS and in the CNS, see Reference [40]. The inventors propose that these physiological and pathological changes in cytoskeletal composition change the viscolelastic properties of axons and contribute to either increase or decrease the axonal resistance to damage.

Within the prior art the substantial majority of studies on axonal degeneration have focused onto the biochemical signaling events triggered by axonal insults. The results obtained by the inventors show that the mechanical properties of axons also play a significant role in deciding the axonal fate after damage and that these cannot be attained from bulk sample measurements or analysis as with biochemical signalling. The ability to growth single axons or small numbers of clustered axons allows for the generation of new, and to the inventor's knowledge, reproducible, and precise models to study the different parameters involved in axonal degeneration. Further the concurrent use of atomic and optical microscopy tools afforded by embodiments of the invention to compress and image simultaneously to assess axonal integrity allow the different events involved in axonal loss such as cell signaling cascades, activity of mechanosensors, and electrostatic changes. The models derived from experimental observations and measurements of single and small number of axons are of particular importance in light of recent debates on the foundation of nerve pulse propagation as an acoustic signal, see Reference [41]. Some scientists claim that the action potential is actually an acoustic pulse or a soliton, see Reference [42]. Along the same lines, other research demonstrates that two-dimensional pressure pulses exist in the lipid layers and are thermodynamic in origin, see Reference [43], and these pulses may play an important role in cell-cell and protein-protein communications. Deformations of membrane etc. using an AFM and subsequent variations in elastic properties should clearly alter the propagation of such waves, opening the door to test these hypotheses, within well controlled sample environments at a scale commensurate to the physical effects themselves. Embodiments of the invention support the growth, presentation, and analysis of neuron/axon samples to explore chemical and physical stresses on neuronal function, damage, or growth and the propagation of action potentials in soft matter.

D: Micro-Fluidic Cell Structure Background

Axonal degeneration after traumatic brain injury or nerve compression caused by expansion of extraneural tissue is considered to be a common underlying cause of temporary and permanent disability. As discussed supra in respect of research data from the inventors analysis of the effect of gradual axonal compression on isolated axons using live imaging techniques requires the provisioning of biological samples that support the growth and provisioning of single axons, small numbers of associated neurons, etc. under defined growth fluidic environmental and chemical conditions in a manner that supports high resolution, small area/volume measurement at scales of a few microns and microliters. In contrast existing models, central or peripheral nerve bundles are either axotomized or crushed, leading to a global axonal injury, glial response, and degeneration.

Accordingly, embodiments of the invention provide for control of the duration and force applied on a precise region of the axon, enabling injury reproducibility and the observation and comparison of individual axons injured equidistantly from the soma at micron resolution. The inventors applied microfluidics, live cell imaging, and AFM to precisely calculate the force required to disrupt the axonal transport without impairing axonal survival, disrupt axonal transport and selectively induce axonal degeneration in isolated axons, and calculate the elastic modulus of DRG and hippocampal axons.

Figure 6:
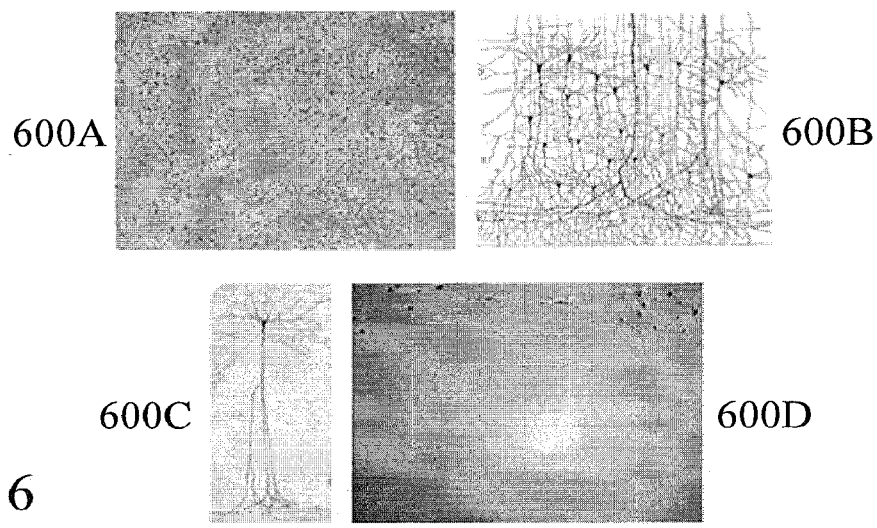
FIG. 6 depicts the efficiency of microfluidic structures according to embodiments of the invention.

It is very hard to study axonal compression in vivo. Axons are surrounded by different types of tissues, veins and arteries, which hamper the evaluation of the single axonal response to compression. In addition, axonal imaging is quite challenging because axons can be very thin, long and form very complex networks inside the brain. Neuronal cultures in vitro organize in a completely different way than in vivo and it is very challenging to differentiate axons and dendrites in vitro. Referring to FIG. 6 there are depicted first to fourth images 600A to 600D respectively demonstrating the efficiency of microfluidic chambers according to embodiments of the invention against the prior art techniques. Referring to first image 600A neurons grown in vitro are depicted having organized randomly whereas in second image 600B neurons are depicted with some degree of organization through directional growth. Third image 600C depicts an image acquired by Santiago Ramon y Cajal for the morphology for neurons grown in vivo which is very similar to that depicted in fourth image 600D for neurons grown within a microfluidic chamber according to an embodiment of the invention.

D1: Design Basis for First and Second Generation Micro-Fluidic Devices

Figure 7:
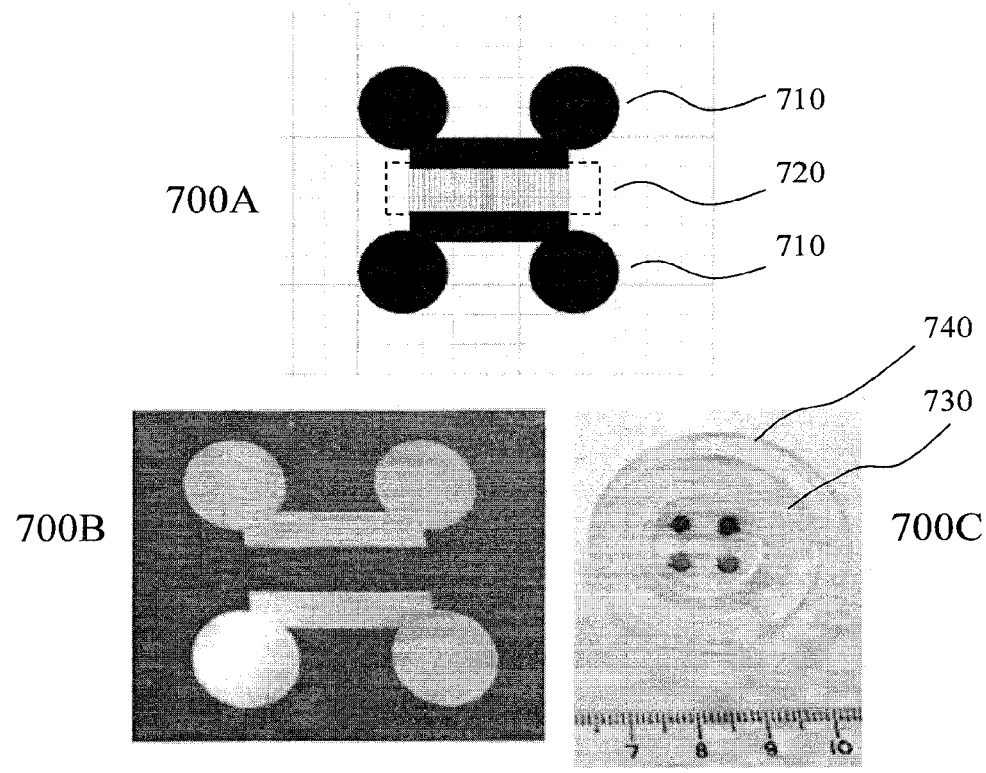
FIG. 7 depicts the design, single mask, and device according to an embodiment of the invention

Using micro-fabrication techniques in conjunction with microfluidics the inventors have established a design presented in first image 700A employing two compartments, depicted by compartments 710 in first image 700A in FIG. 7, that are connected to each other through multiple micro-channels, depicted by region 720 in first image 700A in FIG. 7. Accordingly, the design presented in first image 700A allows for the controlled growth of cells within microfluidic environments allowing investigations of pharmaceutical compounds, pharmaceutical regimes, etc. that interfere with cell adhesion and mobility etc. or can impact the electro-chemical processes within synapses etc. Within the prior art described in the background a similar technology supports solely the study of neurons. However, the inventors have established new designs and design features that allow for the culture of a wider range of cells whilst reducing the volumes of pharmaceuticals and/or cells required whilst supporting extended culture durations and increasing the efficiency of culturing.

Beneficially, embodiments of the invention significantly reduce the volumes required for the medium and pharmaceutical compounds significantly reducing laboratory costs on reagents and samples. Beneficially embodiments of the invention also allow significant reductions in the numbers of cells required both through reductions overall in volume but also through increased retention efficiency within the microfluidic structure thereby significantly reducing the use of animals to provide these cells but also the time spent on cells and reagents preparation. Beneficially, the micro-fluidic structures are also designed for use and exploitation within laboratory conditions without requiring special coatings, special coverslips, or special adapters for measurement and inspection equipment, e.g. optical microscopy.

Beneficially, embodiments of the invention may be employed, based upon design variations for example, to provide structures with the benefits outlined supra and below that support culturing and characterisation over a range of cellular scales from single cells to clusters of cells and ensembles of cells and dimensions from a few microns to thousands of microns.

Referring to FIG. 7 then depicted in second image 700B of the single mask required to fabricate the microfluidic structures according to embodiments of the invention as opposed to the two or more masks within prior art solutions. Also depicted in FIG. 7 in third image 700C is a PMDS microfluidic structure 730 sitting within a glass Petri dish and filled with coloured dye for visual effect only.

Figure 8:
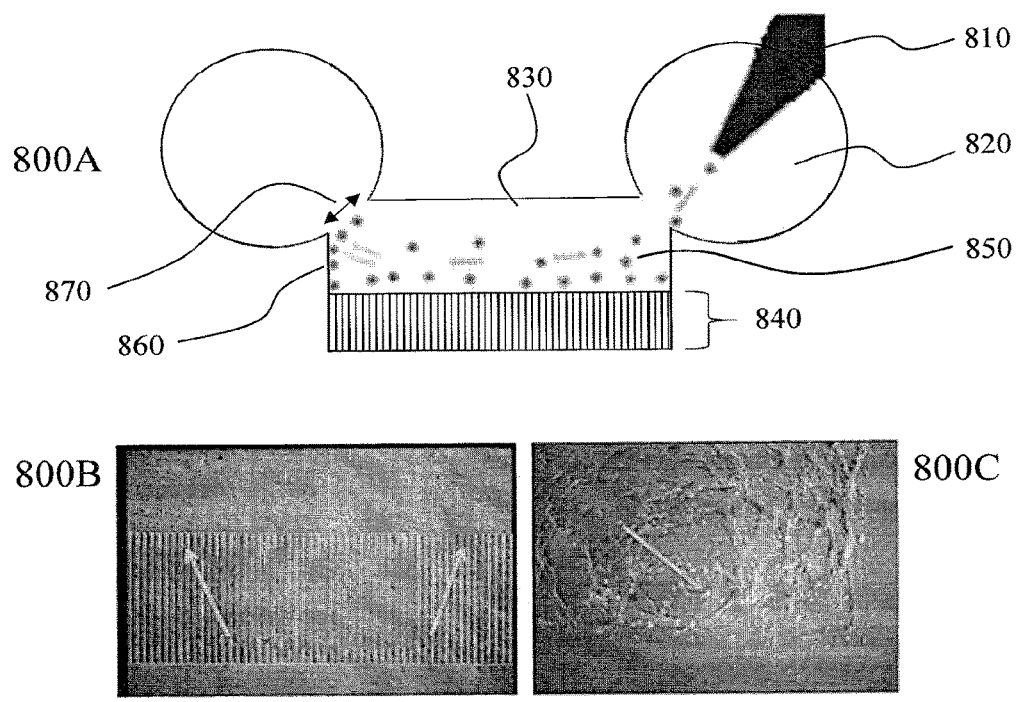
FIG. 8 depicts schematically the addition of cells to a microfluidic structure according to an embodiment of the invention depicting the design feature of wall to channel intersection to enhance cell retention close to the micro-channels.

Referring to FIG. 8 in first image 800A there is depicted a schematic of cell plating a microfluidic structure according to an embodiment of the invention. As depicted one side of a microfluidic structure such as depicted in first image 700A in FIG. 7 is presented comprising first and second wells 820 and connecting chamber 830 together with micro-channels 840 that interconnect the connecting chamber 830 to another connecting chamber, not depicted, and its associated wells. Accordingly, a pipette 810 may be employed to dispense cells 850 within a medium, not shown for clarity.

Within prior art microfluidic devices such as embodied in U.S. Pat. No. 7,419,822 and the other patents referenced within the background, the connecting chamber has a depth of approximately 100 µm in contrast to the depth of the first and second wells, e.g. 3 mm, such that the medium, with cells, flows from the first and second wells, into which the medium is pipetted, to the connecting chamber through hydrostatic pressure. Then the connecting chamber of depth approximately 100 µm is connected to the array of micro-channels whose depth, e.g. 3 µm, is substantially less than the connecting chamber such that again hydrostatic pressure is employed to drive the medium towards the micro-channels. Such a design is depicted in first schematic 1000A and first optical micrograph 1000D in FIG. 10.

In contrast, the micro-fluidic device depicted in first image 700A in FIG. 7 and first image 800A has a depth of approximately 3 mm for the first and second wells 820 such that the medium flows from the well 820 into which the medium is dispensed through the connecting chamber 830 towards the other well 810 at the other end of the connecting chamber 830. However, the depth of connecting chamber 830 and micro-channels 840 within embodiments of the invention are the same such that there is no hydrostatic pressure drive of the medium, and therein the cells, towards the micro-channels. In contrast to the prior art devices which employ smooth low resistance connecting chamber geometries between the first and second wells the connecting chamber 830 according to an embodiment of the invention offers resistance and restriction to fluid flow to increase efficiency of cell, retention at or within the micro-channels. Accordingly, as depicted in first image 800A the exit 870 from the first well 820 into which the fluid is pipetted in narrow relative to the diameter of the well 820. Similarly, the exit 870 from the connecting chamber into the second well 820 is narrow relative to the width of the connecting chamber 830. Additionally, the end wall of the connecting chamber at the ends of the micro-channel arrays has a high angle relative to the fluid flow direction as the medium travels from the first well 820 to the second well 820. Accordingly, the high angle wall 860 and narrow exits 870 results in increased cell retention within the connecting chamber as the medium flows. The result as depicted in second and third images 800B and 800C respectively wherein the inventors have observed an increased number of cells at close to the walls, depicted by blue arrows in second image 800B, and at the entrance of the micro-channels, depicted by arrow in third image 800C.

Beneficially, the inventors can adapt both the cross-section and the length of the micro-channels allow the micro-fluidic structures to be employed in the studies of adhesion and mobility of different cell types. When culturing neurons, for example, cell bodies remain in the connecting compartment 830 into which they are loaded whilst the axons grow and navigate through the micro-channels 840 to the other connecting compartment on the other side of the micro-channels 840. Alternatively, to study parasitology and infectious diseases, host cells can be seeded in one side of the device, parasites into the other side of the device, and pharmaceutical compounds added to one or other side in order to investigate what attracts or inhibits parasite migration through the channels to infect cells. Similarly, embodiments of the invention may be used to study pharmaceutical compounds that inhibit the invasiveness of cancer cells; the immunological cellular response; damage thresholds and/or recovery characteristics of axons, neurons, etc.; and to perform fertility tests by evaluating the motility of sperm cells through the micro-channels. It would be evident that other applications for devices exploiting the techniques described with respect to embodiments of the invention will exist beyond the few described within this patent specification.

Figure 9:
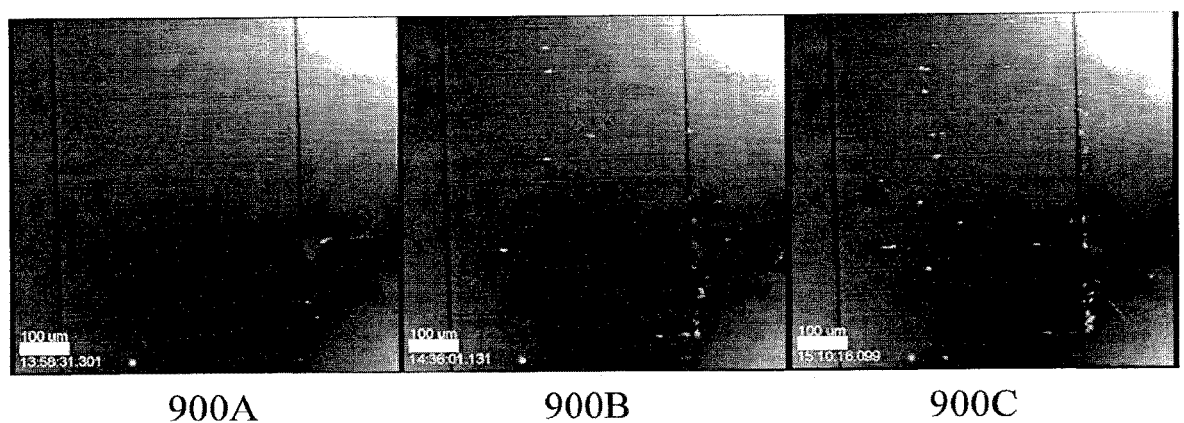
FIG. 9 depicts the application of a microfluidic structure according to an embodiment of the invention to the analysis of Trypanosoma cruzi epimastigotes and attraction to specific human proteins.

One such application is depicted in FIG. 9 through first to third images 900A to 900C of the micro-channel/connecting chamber of a micro-fluidic structure according to an embodiment of the invention with respect to the analysis of Typanosoma cruzi at epimastigote stage, grey spots, which cause Chagas disease in humans and are transmitted through the bite of a mosquito found in Latin America and Southern USA. The parasite gets into the bloodstream and make its nest in the heart, eventually causing the death of the patient due to cardiac insufficiency. First image 900A shows the result of adding the parasite to the right compartment of the micro-fluidic structure and a heart protein to the left compartment. In second image 900B, taken just under 2 minutes after addition of the parasite it is clear that the parasites have started to swim through the channels towards the left compartment, and that in third image 900C the number of parasites in the channels increases while several parasites get stuck at the channels entrance. By adjusting the human protein it is possible to show that the parasites are attracted to specific human protein(s).

Figure 10:
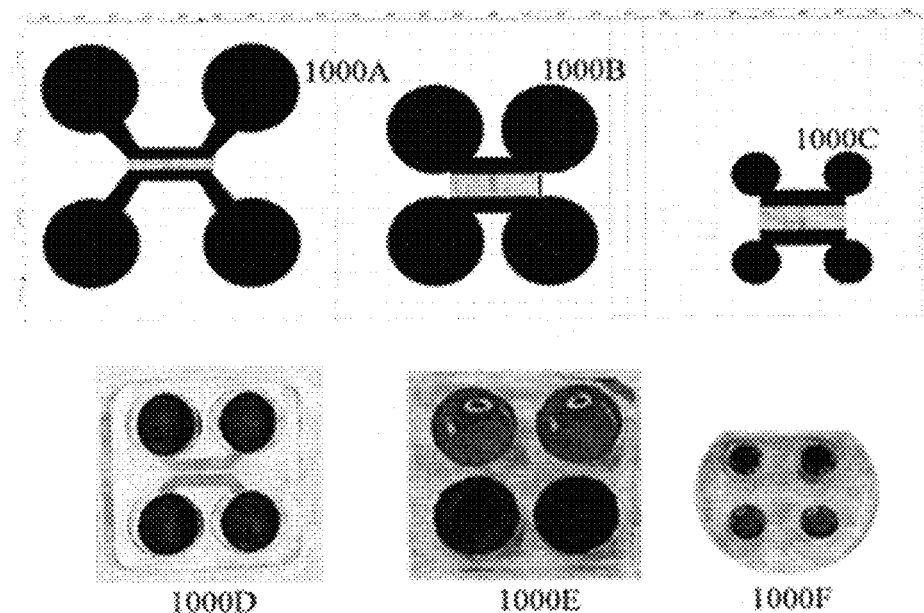
FIG. 10 depicts a prior art micro-fluidic structure with first and second generation microfluidic devices according to embodiments of the invention.

Now referring to FIG. 10 there are depicted first to third images 1000A to 1000C respectively and first to third optical micrographs 1000D to 1000F respectively. First image 1000A and first optical micrograph 1000D depict a micro-fluidic structure according to the prior art of U.S. Pat. No. 7,419,822, hereafter referred to as the 822 Device, variants of which are marketed by Xona Microfluidics. As evident the device has a large footprint with large wells, and low resistance medium flow from one well to the other for either the upper or lower compartment. Second image 1000B and first optical micrograph 1000E depict a micro-fluidic structure according to a first generation of the micro-fluidic structures according to embodiments of the invention in order to mitigate the limitations within the 822 Device. Accordingly, the wells are now connected to the connecting chamber of a micro-fluidic structure with openings directly from the wells to the connecting chamber. This increased cellular retention even absent the exit restrictions.

Third image 1000C and third optical micrograph 1000F depict a micro-fluidic structure according to a second generation of the micro-fluidic structures according to embodiments of the invention in order to mitigate the limitations within the 822 Device. This design is that of first image 700A in FIG. 7 and first image 800A in FIG. 8 wherein a smaller structure is implemented significantly lower the volumes of reagents/medium etc. but absent a commensurate increase in cell placement efficiency fewer cells would be placed in the appropriate relationship to the micro-channels due to the lower number of cells within the medium. However, the restrictions between the wells and connecting chamber coupled with the high angle wall at the end of the connecting chamber results in increased cell retention within the connecting chamber and as a result increased cell placement at the appropriate positions relative to the micro-channels defined from the adhesion promotion materials, which are common to the first generation micro-fluidic device according to an embodiment of the invention and 822 Device prior art also depicted in FIG. 10.

D2: Manufacturing and Design of First and Second Generation Micro-Fluidic Devices A micro-fluidic chamber device according to the second generation design such as depicted in third image 1000C and third optical micrograph 1000F of FIG. 10 consists of a polydimethylsiloxane (PDMS) body containing a relief pattern of two connecting chambers (compartments) connected by micro-channels which, for example may be 10 µm wide, 3 µm high, and 2 mm long. Each compartment consists of a rectangle, also called the main chamber, that is 1.5 mm, 7 mm long, and 100 µm deep which is connected at either end to two 4 mm diameter circles that are punched open to form the wells. Due to the placement of the 4 mm diameter wells the effective opening between the wells and the connecting chamber is a 1.2 mm wide by 100 µm deep. Overall the PMDS device is 12 mm×12 mm such that the PDMS device can be formed within and cut from a 17 mm diameter PMDS rod such that the final device is 3 mm or 4 mm high for example.

Once formed the PMDS device is inverted, mounted onto a glass coverslip to which it adheres such that the micro-channels are formed between the coverslip and the PMDS device. At this point the device can be loaded with the medium containing the cells. This, for example, may be via the upper right circular well, wherein the medium and cells enter the connecting compartment (rectangular main chamber), flow along the connecting compartment and hence along the openings to the micro-channels towards the other well of the device. However, due to the flow pattern and opening position/geometry most cells hit the high angled wall, e.g. 90-degree, and bounce back inside the main connecting chamber thereby impacting other cells moving towards the small exit, 1.2 mm×100 µm, thereby increasing their time within the connecting compartment, slowing and redirecting other cells etc. such that the net result is an increase in the number of cells close to the micro-channels. Once the medium has established etc. then the device can be incubated and cultivated accordingly to the cell type. An example of the detailed cell plating protocol can be found, for example, in Reference [8]. Subsequently, the cultured cells observed, measured, etc.

Beneficially, the micro-fluidic device according to embodiments of the invention exploiting the design methodology described supra in comparison to prior art techniques and the micro-fluidic 822 Device allows:

use of standard glass cover slips and microscope slides as it is smaller and fits within the holder of most microscopes without special adapters;

requires approximately 200 µl of medium compared with 600-800 µl for the 822 Device and 2000 µl (2 ml) for regular cell dishes representing a cost saving in reagents and pharmaceuticals of 75% and 90% respectively;

supports longer micro-channels allowing the imaging of parallel axonal growth and of cell migration and adhesion for longer periods in vitro;

reduced dimensions of the exit/entrance versus the 822 Device, approximately 40% smaller, reduces flow of cells outside the main chamber and increases the adhesion of cells close to the channels;

high angle wall of the main chamber further acts to decrease the cells flowing out of the main chamber such that there is an increase in the amount of the cells close to the channels and a decrease in the number of cells needed;

reduced time analyzing and imaging as all cells are cells are precisely positioned in the array of micro-channels and are all on the same plane and where the cells cannot enter the micro-channels then their positions are defined even further;

transparent micro-fluidic devices can be employed to study optical interactions;

increased channel volumes allow for increased neuron survival, in instances the inventors have imaged neurons upon to 28 days.

Beneficially, the micro-fluidic device according to embodiments of the invention exploiting the design methodology described supra in comparison to prior art techniques and the micro-fluidic 822 Device allows for modification of geometry allowing the micro-fluidic devices to be employed in research and development as well as screening etc. in other biomedical fields including, but not limited, to cancer (oncology), parasitology, infectious diseases, pharmaceutical compounds, fertility testing, and biological fluid filtering.

Considering a prior art regular 35 mm diameter cell culture dish it is necessary to plate 100,000 to 200,000 neuronal cells per dish. With the 822 Device this number is reduced to at least 60,000 cells/dish and with the device of the present invention good results are available with up to 20,000 cells/dish. These numbers may vary according to the cell type, for Dorsal Root Ganglia neurons the device of the present invention just need 5,000 neurons/dish. Taken together these results indicate that the microfluidic structures according to embodiments of the invention can reduce by up to 90% the number of cells needed per experiment. These numbers translate in a large reduction of the number of animals used to prepare primary cultures which is another important benefit in times of increased focus to animal rights and reducing the extent to which animals are employed in many fields of medical research.

The study of neuronal synapses is fundamental to the understanding of neuronal function. Accordingly, such studies are essential in the study and analysis of neurodegenerative diseases, such as Alzheimer's disease or Parkinson's disease, as well as assessments of pharmaceutical treatments etc. Hippocampal neurons in dissociated cell culture are one of the most extensively used model systems in the field of molecular and cellular neurobiology. In primary cultures of rat embryos at embryonic day 19, mature synapses on dendritic spines were seen from day 10 onward, and the number of synapses steeply increased in the third week. Fenestrated or multiple synapses were found after 14 or 21 days, respectively, see for example Reference [45]. Therefore, devices that promote neuronal survival for more than 14 days, such as according to embodiments of the invention, enable the study of neuronal synapses. Experiments by the inventors have demonstrated neuron survival rates over 80% for more than 21 days in culture. In contrast, the 822 Device tested by the inventors exhibit 100% neuron mortality after only 12 days in culture and within the U.S. Pat. No. 7,419,822 it is stated that the viability of neurons is only approximately 50-70% after 7 days in culture.

D3: Design Basis for Third Generation Micro-Fluidic Devices

Figure 11:
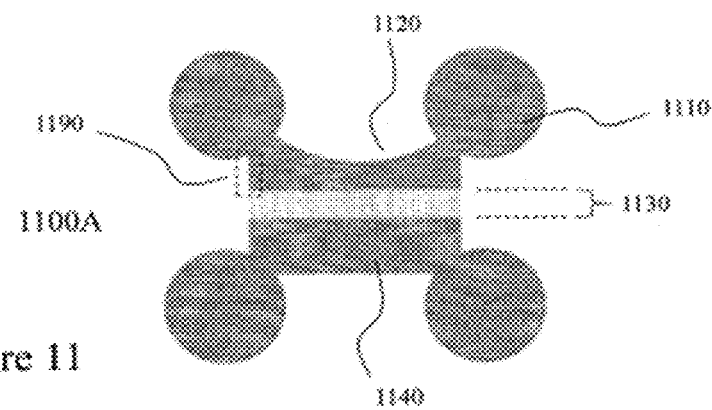
FIG. 11 depicts a third generation microfluidic device according to an embodiment of the invention.

Referring to FIG. 11 there is depicted an image 1100A of a micro-fluidic structure according to a third generation of design according to an embodiment of the invention. Structurally the third generation micro-fluidic structure is similar to that of the second generation micro-fluidic device depicted in FIGS. 7 and 8 together with third image 1000C and third optical micrograph 1000F in FIG. 10. As such it maintains all the benefits of that generation of device including the high, e.g. 90 degree, angles that hinder the flow of the cells out of the main chamber in region 1150 rather than lower angle channel transitions within the prior art 822 Device. These diagonal channels of the 822 Device direct the cell flow towards the opposite well and results in cell adhesion outside the cell chamber and far from the channels.

Accordingly, the micro-fluidic structure contains four wells 1110 disposed in pairs with respect to first and second connecting chambers 1120 and 1140 respectively. Linking the first and second connecting chambers 1120 and 1140 is an array of micro-channels 1130. In contrast to the pair of straight sided connecting channels within the second generation device in order to improve the adhesion of cells close to the micro-channels, the topside of the first connecting chamber 1120 has been profiled, for example, with the shape of a concave arc that directs the medium flow and hence cells towards the channels across the micro-channel array before expanding to couple to the other well on that side of the device. In this manner the high-angle wall sections of the first and second connecting chambers 1120 and 1140 are also maintained, these being shown by region 1150. Optionally, both of the first and second connecting chambers 1120 and 1140 may be profiled according to the experimentation being undertaken and the medium loading. Optionally, the profile may be varied according to one or more factors including, but not limited to the viscosity of the medium, the mobility of the cells, micro-channel opening, cell dimension(s), spacing of micro-channels, number of micro-channels, and volume of medium being loaded.

D4: Manufacturing and Design of Third Generation Micro-Fluidic Devices

Micro-fluidic structures, such as third generation micro-fluidic device have been created using micro-fabrication techniques, such as photolithography, in order to create a master mold with sub-micrometer-resolution. Subsequently, soft lithography is used to replicate third generation micro-fluidic device from the master mold, typically using the silicone polymer polydimethylsiloxane (PDMS). The master molds beneficially for the third generation microfluidic devices employ a single stage process versus the more costly dual stage processing and dual photomasks within the 822 Device. Initially, a photomask is designed, for example using the CleWin layout editor and prepared with ±0.3 µm resolution. As evident from first image 1300A in FIG. 13 the photomask consists of the design shown in FIG. 11, containing a relief pattern of two compartments connected by micro-channels. The micro-channels according to embodiments of the invention may be implemented with varying design parameters including, for example, channel widths in the range 1 µm W 250 µm, lengths varying in the range $0.1 \text{ mm} \leq L \leq 125.0 \text{ mm}$, and height ranging from $1 \text{ µm} \leq H \leq 250 \text{ µm}$. Each of the first and second connecting chambers in essence are rectangles with dimensions, for example, of (W=1.5 mm); (L=7.0 mm); ($10 \text{ µm} \leq H \leq 100 \text{ µm}$) connecting the pair of 4 mm wells. The arc on the first connecting chamber 1120 may, for example, be a circular section of R~8.5 mm although it would be evident that other profiles may be employed including, but not limited to, parabolic, hyperbolic, and elliptical as well as other functions of connecting chamber width with distance along the connecting chamber.

Next, the inventors spin coat sufficient photoresist, e.g. a negative epoxy based negative photoresist such as SU-8, onto a cleaned 6-inch (150 mm) silicon (Si) wafer. The selected photoresist being compatible with thick coating in a single or multiple layer process to the desired thickness of the pattern, e.g. $1 \text{ µm} \leq t \leq 250 \text{ µm}$. The Si wafer is baked for the appropriate time and temperature to achieve the desired thickness and exposed through the high-resolution transparency photomask. After exposure, the wafer is baked on a hot plate and developed with SU-8 photoresist developer. The wafer is treated with a solution to increase hydrophobicity and facilitate removal of the PDMS. The micro-fluidic devices are prepared by adding PDMS to the mold, cure and cut each as cylinders with ϕ=17 mm and Thickness=4 mm. From these the 4 mm circles are punched open to form the wells and an edge of the cylinder is removed to facilitate orientation of the cell loading chamber during experiments. Where PDMS is employed this provides for an optically transparent micro-fluidic device which can be adhered to a glass coverslip thereby providing the enclosing of the micro-channels and sealing the device in place. After incubation of the device with a medium, cells are added and cultivated accordingly to the cell type.

Figure 12:
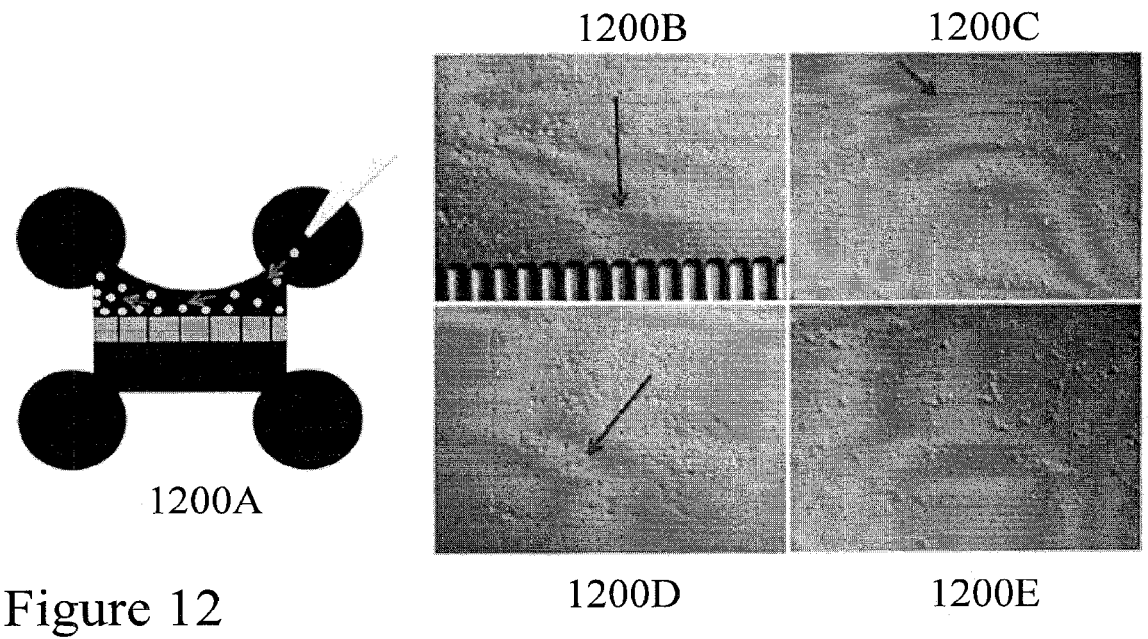
FIG. 12 depict cell plating of a third generation microfluidic device according to an embodiment of the invention together with optical, micrographs of the device in use.

These cells are added, as depicted in FIG. 12 in first image 1200A, into the upper right well, top right circle, and therein enter the upper connecting compartment, also referred to as the main chamber, though a 1.2 mm opening and of depth equal to that of the structure, e.g. 50 µm. These therefore flow through the upper connecting compartment and are directed by its profile towards the micro-channels and are retained either within the micro-channel and/or connecting compartment according to the design of the micro-channel and dimensions of the cell. Optionally, a material such as Poly-D-Lysine (PDL), Poly-L-Lysine (PLL), laminin, or any other extracellular matrix component(s) may be used to enhance cell attachment to the glass coverslip, plastic and glass, surfaces. For many anchorage-dependent cells, the nature of the culture substrate has a major effect on cell growth and the requirement for serum proteins. These cells flow within the upper connecting compartment and, flow in the direction of the opposite well (top left circle). Most cells hit the high angled wall and bounce back inside the main chamber being trapped inside the cell chamber and increasing the number of cells close to the micro-channels. This being depicted schematically within first image 1200A by the pipette in the upper right well, the cells depicted as dots and their motion by red arrows.

Exploiting a micro-fluidic device according to an embodiment of the invention rat hippocampal neurons were plated as depicted in second image 1200B and as the arrow shows, most neurons adhere closer to the channels and fewer to the edge of the concave arc edge of the connecting channel as evident in third image 1200C. Fewer neurons adhere close to the concave arc (arrow) because it pushes cells closer to the channels. The high angle walls block the cell flow and keep cells inside the cell-loading chamber, resulting in more cells close to the channels, as evident in fourth image 1200D. Overall, as evident in fifth image 1200E these reduce the number reaching the other well and accordingly these features together increase the efficiency of the device and reduce the number of cells needed/experiment. In addition, according to the design of the microchannels etc. these designs according to embodiments of the invention promote neuronal survival for longer periods. The second to fifth images 1200B to 1200E depict primary rat hippocampal neurons after 15 days in culture growing inside the devices.

Figure 13:
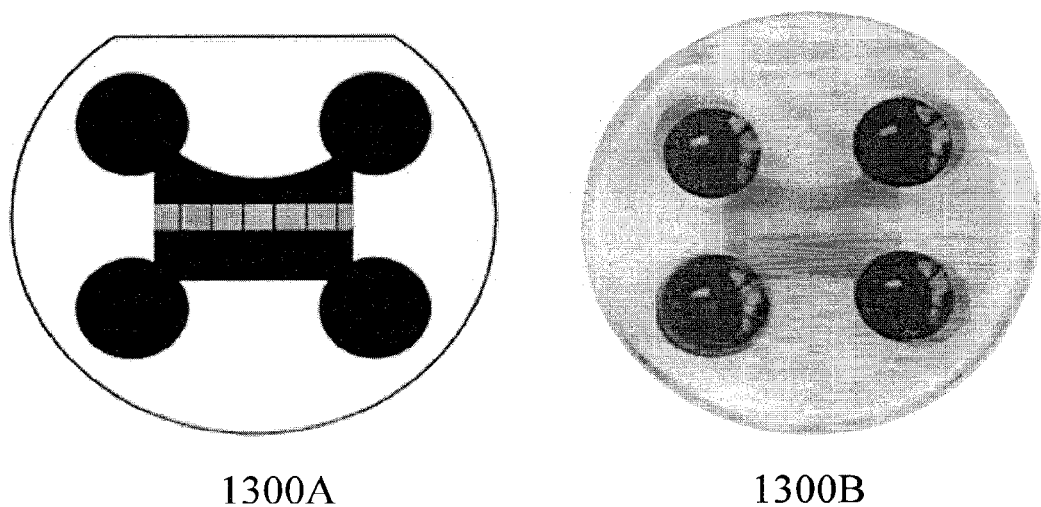
FIG. 13 depicts schematic and fabricated device with dye loading.

FIG. 13 in first image 1300A depicts the mask design for a micro-fluidic device according to an embodiment of the invention whereas second image 1300B depicts an as fabricated micro-fluidic device that has been loaded with red dye to show the micro-fluidic structures within the otherwise transparent PDMS device.

Figure 14:
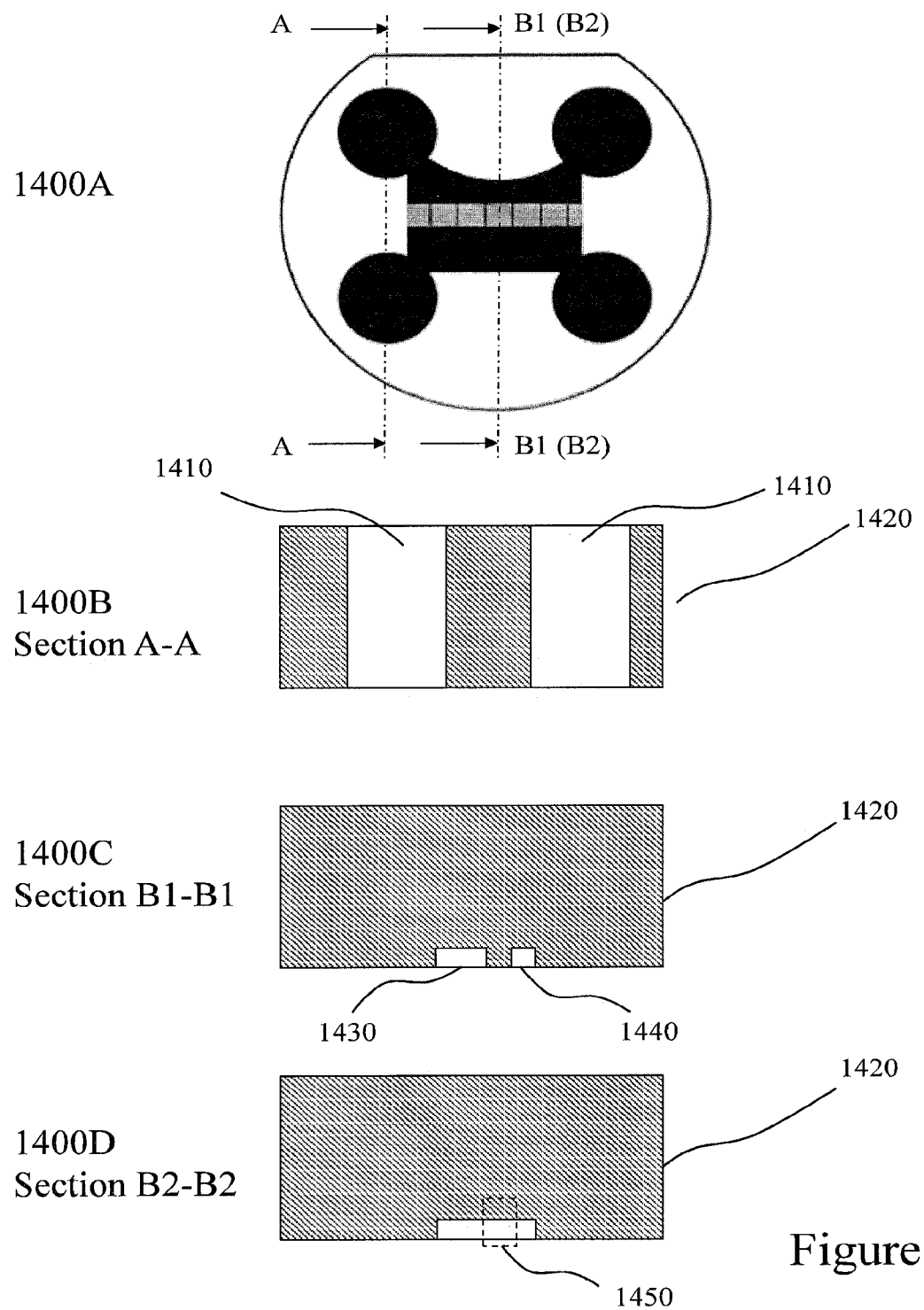
FIGS. 14 and 15 depict third generation microfluidic devices according to embodiments of the invention.

Referring to FIG. 14 there are depicted plan view 1400A, first cross-section A-A 1400B, second cross-section B1-B1 1400C, and third cross-section B2-B2 1400D for a third generation micro-fluidic device according to an embodiment of the invention wherein the device comprises wells 1410 within the body 1420. Coupled to the upper and lower pairs of wells 1410 are first and second connecting compartments 1430 and 1440 of depth t(1), depicted in second cross-section B1-B1 1400C and micro-channels 1450 also of depth 41) as depicted in third cross-section B2-B2 1400D. Accordingly, in this embodiment of the invention the first and second connecting compartments 1430 and 1440 have the same depth as the micro-channels 1450.

Figure 15:
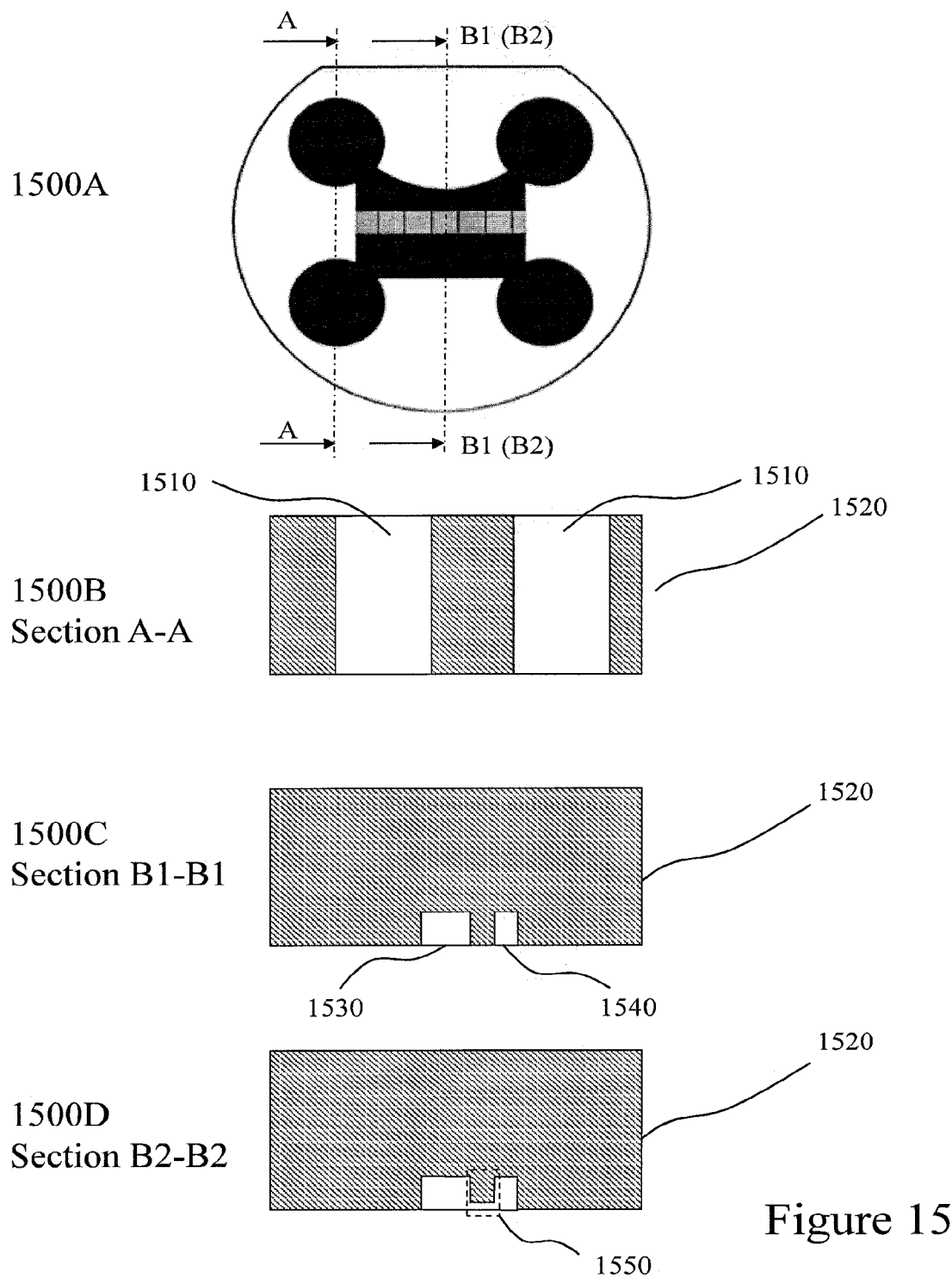

Referring to FIG. 15 there are depicted plan view 1500A, first cross-section A-A 1500B, second cross-section B1-B1 1500C, and third cross-section B2-B2 1500D for a third generation micro-fluidic device according to an embodiment of the invention wherein the device comprises wells 1510 within the body 1520. Coupled to the upper and lower pairs of wells 1510 are first and second connecting compartments 1530 and 1540 of depth t(1), depicted in second cross-section B1-B1 1500C and micro-channels 1550 also of depth t(2)<t(1) as depicted in third cross-section B2-B2 1500D. Accordingly, in this embodiment of the invention the first and second connecting compartments 1530 and 1540 have a depth greater than the depth of the micro-channels 1550. It would be evident that in a further embodiment of the invention the first and second connecting compartments 1530 and 1540 may have a depth less than that of the micro-channels 1450, i.e. t(2)>t(1).

Figure 16:
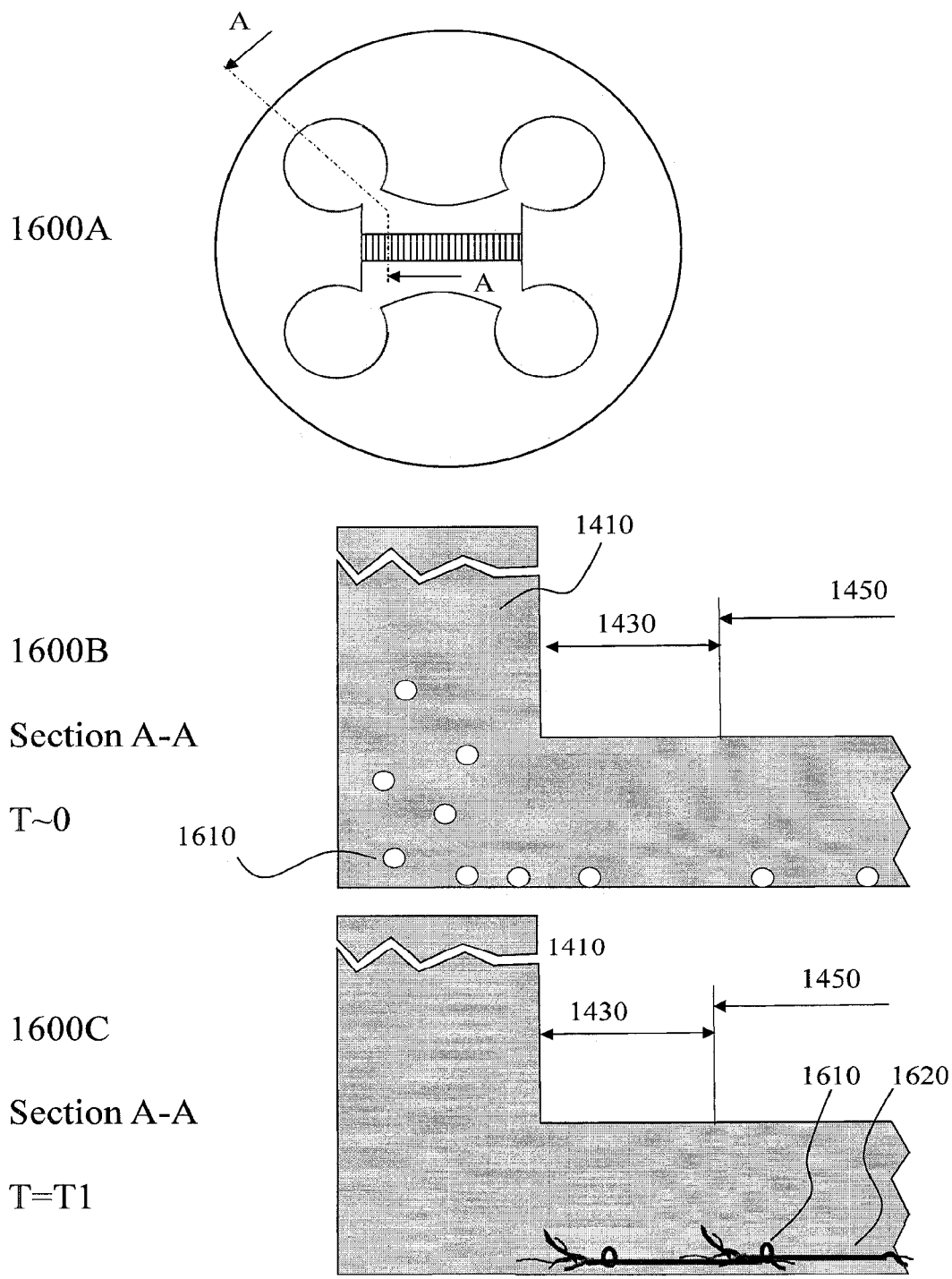
FIG. 16 depicts a cross-section of a third generation microfluidic device according to embodiments of the invention at initial cell loading and post-culturing.

Referring to FIG. 16 there is depicted plan view 1600A and first and second cross-sections 1600B and 1600C with respect to a third generation micro-fluidic device according to an embodiment of the invention such as depicted in FIG. 14 wherein the first and second connecting compartments 1430 and 1440 and micro-channels 1450 all have depth t(1)>t(3), where t(1) is the depth of the micro-fluidic device elements and t(3) is the height of the cells 1610 being analysed, characterised, experimented upon. Accordingly, the cells introduced into the wells 1410 may flow through the first connecting compartment 1430 into the micro-channels 1450 wherein they may be cultivated such that for example the neurons 1610 extrude axons, and dendrites (not shown for clarity). In this variant multiple neurons may be disposed within a single micro-channel such that the axons/dendrites of a small number of neurons may be analysed. Additionally, the volume of medium surrounding the neurons allows them to be cultivated for substantially longer. The inventors have demonstrated cultures to date up to 28 days.

It would be evident from second cross-section B1-B1 1400C and third cross-section B2-B2 1400D in FIG. 14 and first and second cross-sections 1600B and 1600C respectively in FIG. 16 that the first and second connecting compartments 1430 and 1440 and the micro-channels 1450 are all formed with the same depth 41). Accordingly, the hydrostatic pressure within the first and second connecting compartments 1430 and 1440 and the micro-channels 1450 are the same such that there is no hydrostatic pressure differential driving the medium and/or cells within the device. Beneficially as evident from FIG. 19 embodiments of the invention without hydrostatic pressure as depicted in FIGS. 8, 14, and 16 may be manufactured using a single photolithography/etching process with a single photomask.

In contrast, it would be evident from second cross-section B1-B1 1500C and third cross-section B2-B2 1500D in FIG. 15 that the first and second connecting compartments 1530 and 1540 are formed with a depth t(1) that is greater than the micro-channels 1550, which have a depth t(2)<41). Accordingly, the hydrostatic pressure within the first and second connecting compartments 1530 and 1540 is different to that within the micro-channels 1550 and accordingly there is a hydrostatic pressure differential driving the medium and/or cells within the device. The magnitude of this hydrostatic pressure differential may be varied by design. This configuration is that employed within the prior art devices, e.g. the 822 Device, wherein the implementation for commercial sale by Xona Microfluidics has t(2)=3 μm<t(1)=100 μm.

Now referring to FIG. 17 there is depicted a cross-section A-A of micro-fluidic structure 1700A in second image 1700B of a third generation micro-fluidic device according to an embodiment of the invention wherein the dimensions of the micro-channels and profile of the micro-channels have been varied with respect to the cell as depicted in first to fifth channel groups 1710 to 1750 respectively. Fifth group 1750 may be formed through a different process than those described supra in respect of PDMS and photomask such as through the etching of silicon or the manufacturing of a metal mold for stamping a biocompatible material prior to final curing for example.

Referring to FIG. 18 there are depicted first to fourth images 1800A to 1800D of a third generation micro-fluidic device according to an embodiment of the invention wherein there are depicted the upper perspective view of the fabricated micro-fluidic device, lower perspective view of the fabricated micro-fluidic device, the fabricated micro-fluidic device mid-assembly with a glass cover slip and a plan view of assembled device respectively.

Figure 19:
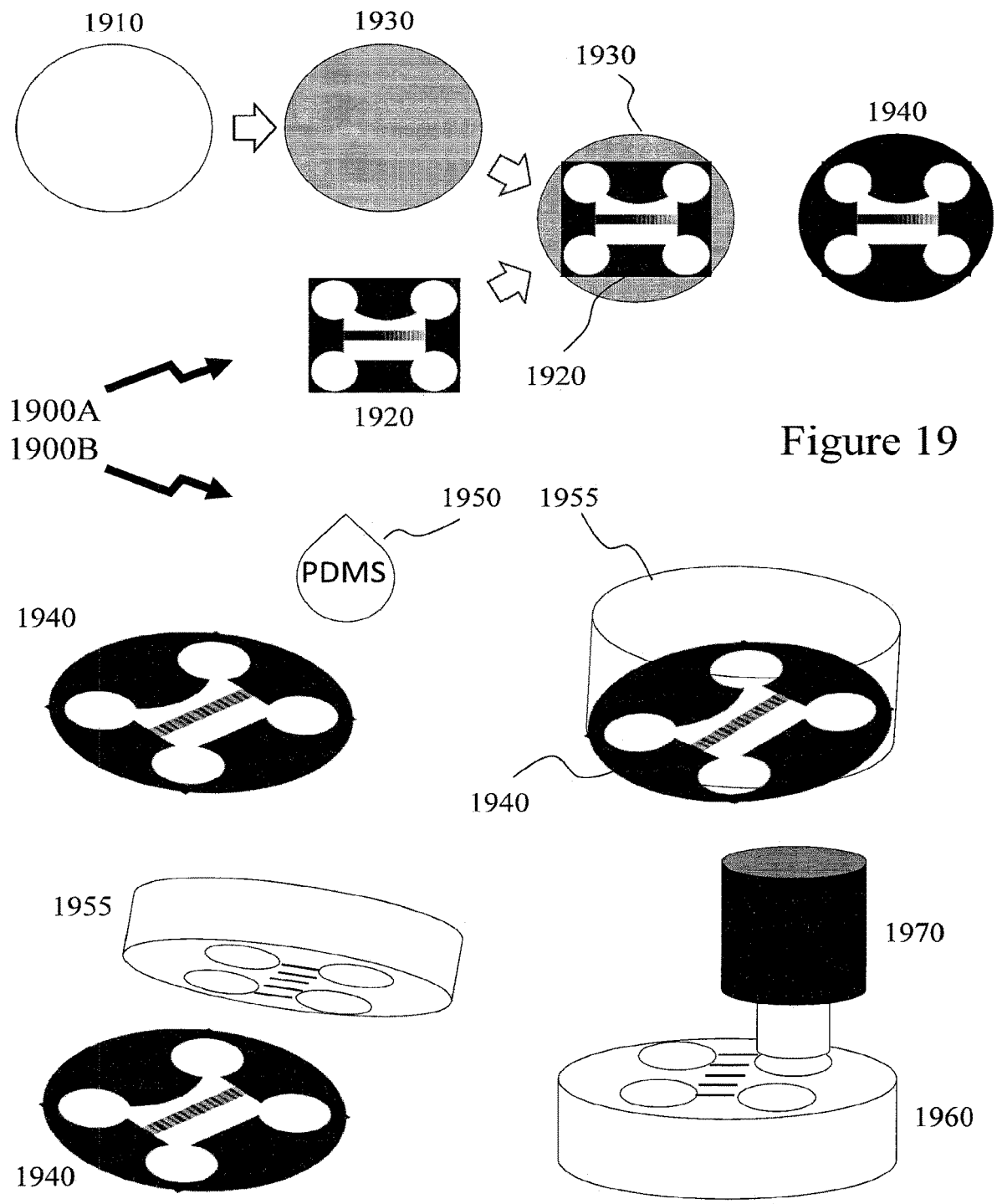
FIG. 19 depicts exemplary process flows for fabricating a master mold and subsequently molding microfluidic devices for structures according to embodiments of the invention.

Now referring to FIG. 19 there are depicted schematically first and second exemplary process flows 1900A and 1900B for fabricating a master mold and subsequently molding microfluidic devices for structures according to embodiments of the invention respectively. Accordingly, in first exemplary process flow 1900A a silicon wafer 1910 is spin coated with photoresist 1930 wherein it is brought into alignment with a photomask 1920 that has been previously manufactured defining the micro-fluidic structure and the photoresist 1930 exposed. Subsequently, after chemical processing to remove exposed resist and etching the silicon wafer, a master mold 1940 is formed. Whilst a single micro-fluidic structure is depicted it would be evident that according to the diameter of the silicon wafer 1910 and the footprint of the micro-fluidic structure that multiple micro-fluidic structures of a single design or of multiple designs may be fabricated simultaneously. Subsequently, the master mold 1940 as depicted in second process flow 1900B is used to manufacture micro-fluidic devices for culturing applications.

Accordingly, as depicted PDMS 1950 being a flowable polymeric organosilicon prior to its curing is poured, spun, or otherwise disposed atop the master mold 1940 and cured thereby yielding PDMS block 1955. This may, for example, be formed and cured at its final thickness or formed/cured in a series of steps. Subsequently, this PDMS block 1955 is removed from the master mold 1940. However, at this point it has the surface topology of the master mold and hence contains the micro-channels and connecting chambers together with only shallow moldings for the wells. These provide alignment features for the punch 1970 to punch through the soft PDMS in order to form the wells of the micro-fluidic structure. Alternatively, rather than punching to the full depth of the wells a PDMS block 1955, or block formed from another molded material employed, may be formed at a thickness below that of the final well and aligned to another structure to provide the remaining portion of the wells.

Figure 20:
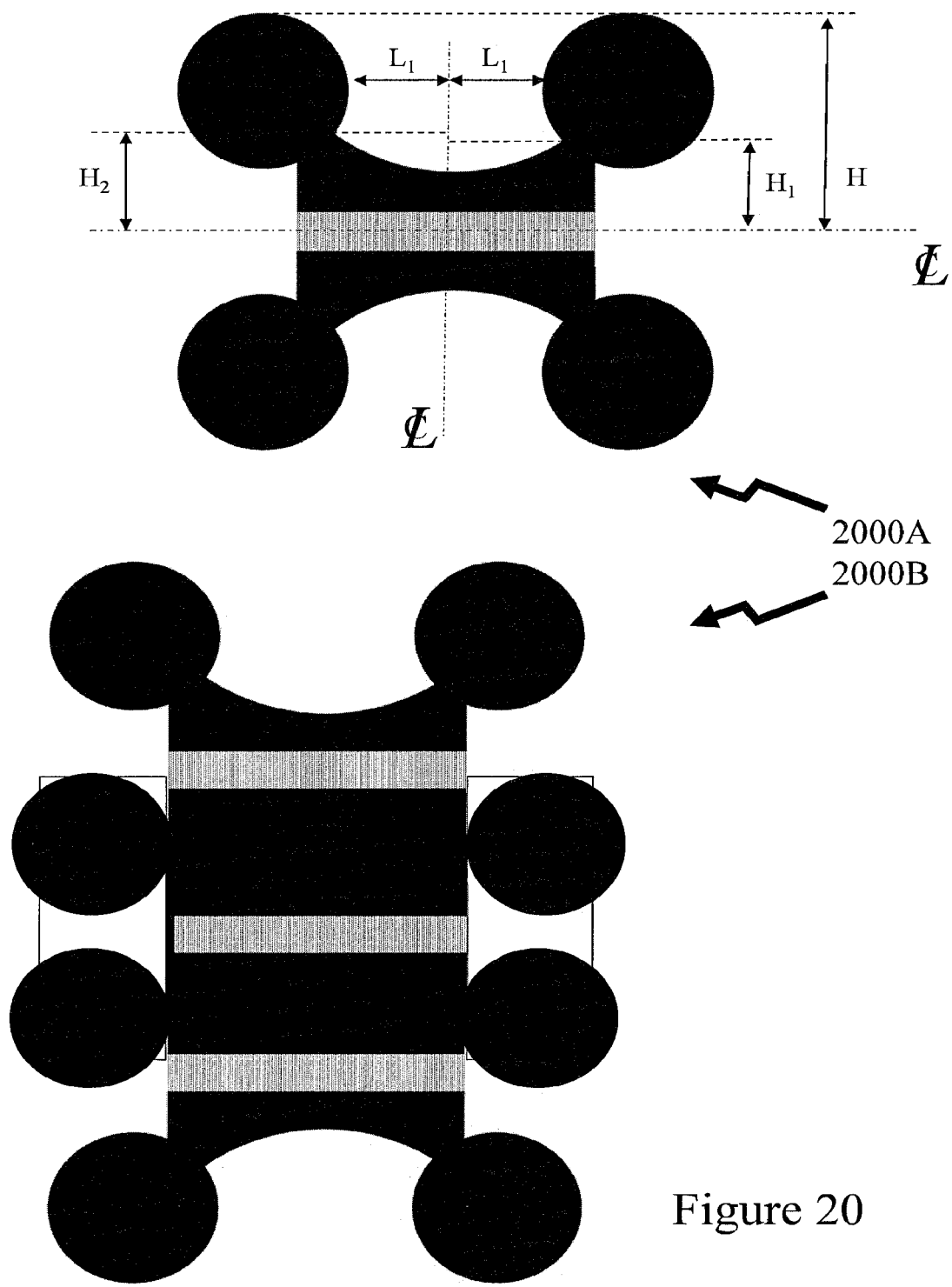
FIG. 20 depicts a micro-fluidic device and an arrayed culture structure according to an embodiments of the invention.

Referring to FIG. 20 there are depicted a micro-fluidic device 2000A and an arrayed culture structure 2000B according to an embodiments of the invention. As depicted the micro-fluidic device 2000A employs the curved upper connecting chamber wall and high angle end wall concepts as described supra in respect of embodiments of the invention, in common with plan view 1600A in FIG. 16 and micro-fluidic structure 1700A in FIG. 17. As depicted the upper wells of the micro-fluidic device 2000A are both offset the same distance from the centerline of the micro-channel array, in this instance their upper edges are both a distance H from the centerline. However, the vertical distances of the upper curved wall profile where it meets the well whilst at common horizontal distance $L_1$ have vertical distances $H_1$ and $H_2$ respectively for the right and left wells. Accordingly, the curved profile of the upper wall may be either laterally offset relative to the vertical centerline of the micro-fluidic device 200A or have different geometry to the right and left hand sides of the device. Accordingly, the entrance/exit may be asymmetric also in width as well as the extent of, the high angle wall being different on the left versus the right side of the micro-fluidic device 2000A. Accordingly, the loading of the cells within the micro-fluidic device 2000A may be "handed" in that they should be loaded into either the left or right hand well. Optionally, the lower compartment may be similarly "handed", reverse "handed" or non-"handed."

Referring to arrayed culture structure 2000B there are depicted at the top and bottom cell loading structures in common with micro-fluidic device 2000A. Disposed between these are another pair of connecting chambers, a set of micro-channels and additional wells. Optionally, cells may be solely loaded into the uppermost and lowermost chambers for retention relative to the micro-channels and culturing. Alternatively, cells may also be provided within the middle connecting chambers or alternatively other cells, fluids, media, etc., may be provided.

Figure 21:
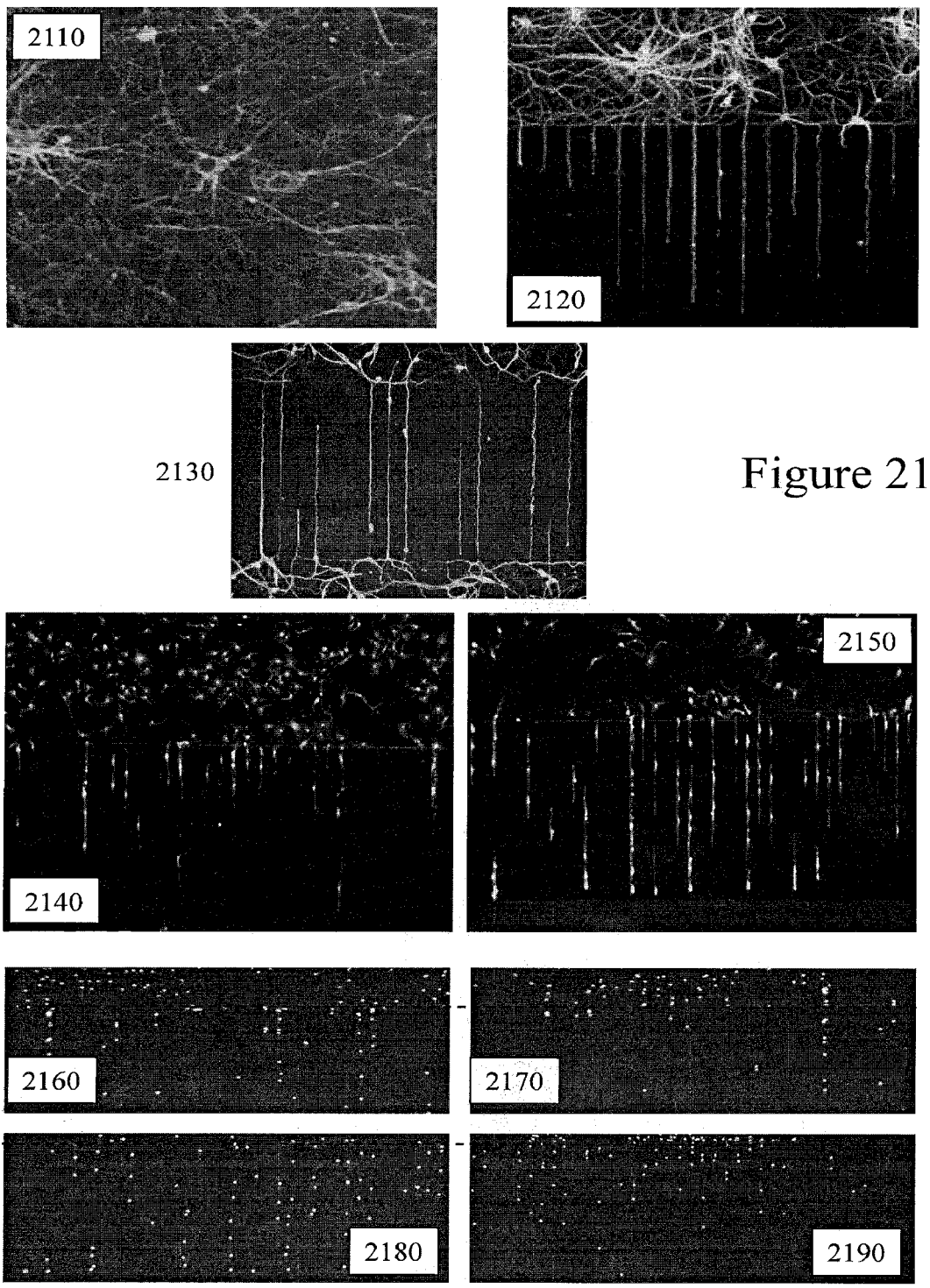
FIGS. 21 and 22 depict cellular analysis of cultures grown with micro-fluidic devices and structures according to embodiments of the invention.
Figure 22:
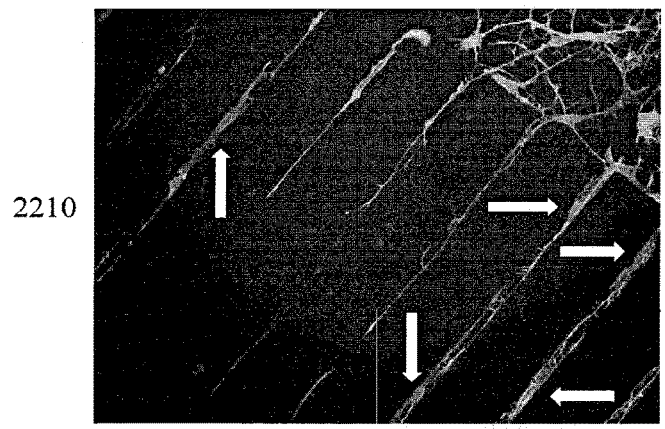
Figure 22:
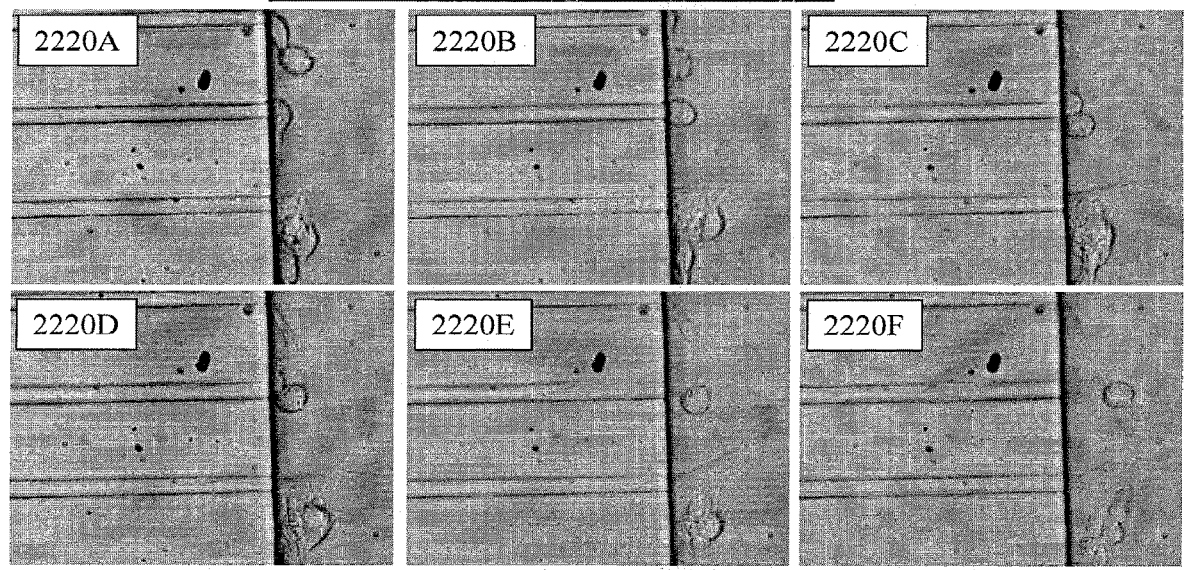
Figure 22:
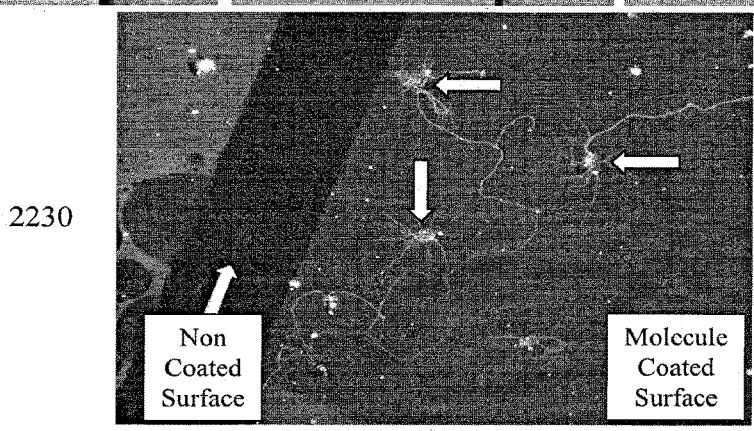

Within the descriptions supra in respect of embodiments of the invention emphasis has been primarily placed upon neurons and axon growth within the micro-channels. However, as described supra the design variations of the micro-channels in terms of length, width, depth, etc. provides opportunity for micro-fluidic devices according to embodiments of the invention to be employed within a variety of research disciplines including, but not limited to, neurology, oncology, and parasitology as well as routine tests and procedures, e.g. fertility testing. This is in addition to the ability to provide environments supporting culturing for period up to and in excess of 21 days. Referring to FIGS. 21 and 22 there are depict cellular analysis of cultures grown with micro-fluidic devices and structures according to embodiments of the invention.

With respect to FIG. 21 there are depicted:
First and second images 2110 and 2120 Rat hippocampal neurons cultured for 18 days on a regular dish (2110) and micro-fluidic chamber (2120). The neurons were labeled using anti-B3tubulin 488 and anti-MAP2 574 and indicated cell survival and healthy cells for more than 2 weeks in culture together with the further benefits of cell organization similar to in vivo; standardization of cultures and results; and faster imaging; above and beyond those previously defined.
Third image 2130 depicts human cortical neurons (embryonic week 20) cultured in vitro inside a microfluidic chamber according to an embodiment of the invention for 21 days and stained with Cell Tracker (Invitrogen)

wherein neurons were plated on both sides of the device to improve synapse formation inside the microchannels.

Fourth and fifth image 2140 and 2150 depicting human microglia cells plated in the devices in the presence (right) and absence (left) of a molecule that triggers microglia activation and migration. Accordingly, microglia cells invasion and migration into the channels is stimulated in the presence of microglia activators.

Sixth to tenth images 2160 to 2190 depict the addition of human microglia cells to one compartment of the devices and different molecules were added to the second compartment to evaluate which molecules triggers microglia activation and migration. Microglia plays a pivotal role in central nervous system immunity and participate in all phases of the multiple sclerosis (MS) disease process. Beneficially, the micro-fluidic structure according to embodiments of the invention thereby provides easy quantification and standardization of results, facilitating the comparison of different molecules and their effects on CNS immunological response.

With respect to FIG. 22 there are depicted:

First image 2210 depicting chicken dorsal root ganglia cells plated and cultured in micro-fluidic devices according to embodiments of the invention for 14 days after which olygodendrocyte precursor cells (OPC) were added to study myelination. Arrows point to the nuclei of OPCs. After 28 days in culture cells were fixed and labeled with cell tracker green (Invitrogen) and nuclei were labeled with DAPI blue (Invitrogen). Accordingly, embodiments of the invention support the co-culture of 1, 2 or more cell types and how to study myelinating cells (OPCs) migration on top of axons.

Second to seventh image 2220A to 2220F depict the microchannels of the device were coated with collagen and human glioma cells (brain cancer cells) were added to one compartment of the device. Cancer cell invasion and migratory potentials are very important for patient diagnostics and treatment. The device according to an embodiment of the invention provides quick access and quantification of these cancer cell aspects. Arrows show the migration of one cancer cell towards the channel and subsequent invasion of the microchannels, mimicking cancer cells behavior in blood vessels and lymphatic vessels, enabling the study of metastasis and testing of new drugs and therapies in very small volume.

Eighth image 2230 depicts the use of pharmaceutical compounds to coat surfaces wherein a molecule that promote axonal growth was added to the device enabling the coating of a pattern on the dish surface. The device was removed and rat DRG neurons were added to the dish, revealing that neurons (arrows) prefer to adhere and to grow on the molecule patterned surface and not in non-coated area (black).

E. Embodiments and Options

Embodiments of the invention have been described with respect to polydimethylsiloxane (PDMS) using the Dow Corning™ Sylgard™ 184 silicone elastomer system. As discussed PDMS is commonly used as a stamp resin in the procedure of soft lithography, making it one of the most common materials used for flow delivery in microfluidics chips. The process of soft lithography consists of creating an elastic stamp, which enables the transfer of patterns of only a few nanometers in size onto glass, silicon or polymer surfaces. The stamp is produced from the normal techniques of photolithography or electron-beam lithography. PDMS may be employed in micro-fluidics on both organic and inorganic contexts. Silicon wafers are commonly used to design channels, and PDMS is then Hydrophilic surface modification may be conducted using plasma etching techniques. Once surface bonds are disrupted, usually a piece of glass slide is placed on the activated side of the PDMS (the side with imprints). Once the bonds relax to their normal state, the glass is permanently sealed to the PDMS, thus creating a waterproof channel.

Optionally, other polymeric organosilicon compounds that are commonly referred to as silicones, may be employed. These may include, but not be limited, those referred to as medical grade silicones in the non-implantable, short-term implantable, and long-term implantable categories.

Optionally, the micro-fluidic structure may be formed through molding and/or casting from a master template.

Optionally, the micro-fluidic structure may be formed by chemical etching of amorphous and/or crystalline substrates including, but not limited to, silica, silicon, quartz, etc.

Optionally, the connecting chambers and micro-channels may be formed from a single step of the manufacturing process, e.g. etching, molding, casting, exploiting a single photolithography stage and single photomask.

Optionally, hot stamping of glass during float processes etc. may be provided to yield stamped glass micro-fluidic devices.

Optionally, biocompatible materials including, but not limited to, ceramics such as alumina and zirconia may be employed.

Optionally a variety of polymers including, but not limited to, poly(ethylene), poly(vinyl chloride), polyurethanes, and polylactides.

Optionally, natural polymers may be employed including, but not limited to, collagen, gelatin, elastin, and polysaccharide Embodiments of the invention relate to microfluidic devices comprising first and second compartments connected by micro-channels, each compartment consisting of a main chamber connected to first and second auxiliary rooms.

Embodiments of the invention relate to microfluidic devices wherein a main chamber of the microfluidic device comprises a corner at each end of an end wall closest to an array of micro-channels along a sidewall of the main chamber, wherein the main chamber has at the other corners of the end walls the first and second auxiliary rooms and the corner have a high angle relative to the sidewall of the main chamber with micro-channels. Optionally, the high angle is between 70 degrees and 110 degrees, between 80 degrees and 100 degrees, and between 85 degrees and 95 degrees, and is 90 degrees.

Embodiments of the invention relate to microfluidic devices wherein the end walls are substantially perpendicular to the direction of flow from the main chamber to the auxiliary room at that end. Optionally, only one end wall has such an angle. Preferably, the end walls decrease the chances of cells added to the micro-fluidic device and flowing from the first auxiliary room the second auxiliary room flowing out of the main chamber.

Embodiments of the invention relate to microfluidic devices wherein the main chamber has a substantially rectangular form.

Embodiments of the invention relate to microfluidic devices wherein the main chamber has a second sidewall substantially opposite the sidewall with the micro-channels wherein the second sidewall has a profile designed to direct fluid flowing from the first auxiliary room towards the other sidewall with the micro-channels. Optionally, the regions upon an upper and/or lower surface within and/or in front of the micro-channels have a coating intended to promote retention of cells within the fluid flowing from the first auxiliary room to the second auxiliary room.

Optionally, the sidewall have the profile is of constant radius, has a profile that is a predetermined portion of at least one of an ellipse, a parabola, a hyperbola, a circle, and a predetermined mathematical function.

Embodiments of the invention relate to microfluidic devices wherein the first and second auxiliary rooms may have circular cross-section and be of a depth substantially higher than the main chamber and/or micro-channels. Optionally, the first and second auxiliary rooms have a cross-section that is at least one of square, triangular, rectangular, elliptical, and polygonal. Optionally, the laterals dimensions of the second auxiliary room are the same as those of the first auxiliary room, are approximately those of the first auxiliary room, smaller than those of the first auxiliary room, and larger than those of the first auxiliary room.

Optionally, the auxiliary rooms have a thickness between 1 mm and 10 mm, between 2 mm and 6 mm, between 3 mm and 5 mm, and between 3.5 mm and 4.5 mm.

Embodiments of the invention relate to microfluidic devices wherein the micro-fluidic device comprises micro-channels that are at least one of rectangular, square, triangular, U-shaped, and V-shaped. Optionally, the micro-channels have a length between 0.1 mm and 125 mm, 0.2 mm and 50 mm, 0.25 mm and 10 mm, and 0.5 mm and 5 mm. Optionally, the micro-channels are straight, curved, meandering, constant cross-section, and variable cross-section, and stepped cross-section. Optionally, the micro-channels have a height between 1 µm and 250 µm, between 1 µm and 100 µm, between 2 µm and 25 µm, and between 3 µm and 10 µm. Optionally, the micro-channels are dimensioned to prevent ingress of a cell being cultured, are dimensioned to allow ingress of a cell being cultured, and are dimensioned to allow growth from the cell within the micro-channel. Optionally, the micro-channels are dimensioned to support the culture of a cell for a minimum of 1 day, for a minimum of 5 days, for a minimum of 7 days, for a minimum of 14 days, and a minimum of 28 days.

Embodiments of the invention relate to microfluidic devices wherein the device is fabricated by a process requiring only a single photomask and/or photolithography stage. Optionally, fluidic micro-channels may be formed with a process such that their depth matches the height of corresponding features on the single photomask.

Embodiments of the invention relate to microfluidic devices comprising first and second compartments connected by micro-channels, each compartment consisting of a main chamber connected to first and second auxiliary rooms wherein the opening between the main chamber and an auxiliary room is designed to limit flow of a fluid within the microfluidic device. Optionally, the opening is substantially smaller than the dimensions of the auxiliary room to which it connects. Optionally, the opening between an auxiliary room and the main chamber is between 0.1 mm and 3.0 mm, between 0.5 mm and 2.5 mm, between 0.75 mm and 2.0 mm, and between 1.00 mm and 1.5 mm 2a 1 to 1.4 mm opening.

F. References

[1]. Maxwell, W. L., J. T. Povlishock, and D. L. Graham. 1997. A mechanistic analysis of nondisruptive axonal injury: a review. J. Neurotrauma. 14:419-440.

[2]. Coleman, M. 2005. Axon degeneration mechanisms: commonality amid diversity. Nat. Rev. Neurosci. 6:889-898.

[3]. Weiss, P., and H. B. Hiscoe. 1948. Experiments on the mechanism of nerve growth. J. Exp. Zool. 107:315-395.

[4]. Adams, J. H., D. Doyle, D. R. McLellan. 1989. Diffuse axonal injury in head injury: definition, diagnosis and grading. Histopathology. 15:49-59.

[5]. Povlishock, J. T. 1992. Traumatically induced axonal injury: pathogenesis and pathobiological implications. Brain Pathol. 2:1-12.

[6]. Smith, D. H., and D. F. Meaney. 2000. Axonal damage in traumatic brain injury. Neuroscientist. 6:483-495.

[7]. Park, J. W., B. Vahidi, N. L. Jeon. 2006. Microfluidic culture platform for neuroscience research. Nat. Protoc. 1:2128-2136.

[8]. Lucido, A. L., F. Suarez Sanchez, D. R. Colman. 2009. Rapid assembly of functional presynaptic boutons triggered by adhesive contacts. J. Neurosci. 29:12449-12466.

[9]. Banker, G., and K. Goslin. 1988. Developments in neuronal cell culture. Nature. 336:185-186.

[10]. Costa, K. D., A. J. Sim, and F. C. P. Yin. 2006. Non-Hertzian approach to analyzing mechanical properties of endothelial cells probed by atomic force microscopy. J. Biomech. Eng. 128:176-184.

[11]. Radmacher, M., R. W. Tillmann, H. E. Gaub. 1992. From molecules to cells: imaging soft samples with the atomic force microscope. Science. 257:1900-1905.

[12]. Mahaffy, R. E., S. Park, C. K. Shih. 2004. Quantitative analysis of the viscoelastic properties of thin regions of fibroblasts using atomic force microscopy. Biophys. J. 86:1777-1793.

[13]. Puttock, M. J., and E. G. Thwaite. 1969. Elastic Compression of Spheres and Cylinders at Point and Line Contact. Commonwealth Scientific and Industrial Research Organization, Melbourne, Victoria, Australia 64.

[14]. Povlishock, J. T., and C. W. Christman. 1995. The pathobiology of traumatically induced axonal injury in animals and humans: a review of current thoughts. J. Neurotrauma. 12:555-564.

[15]. Maxwell, W. L., and D. I. Graham. 1997. Loss of axonal microtubules and neurofilaments after stretch-injury to guinea pig optic nerve fibers. J. Neurotrauma. 14:603-614.

[16]. Kilinc, D., G. Gallo, and K. A. Barbee. 2008. Mechanically-induced membrane poration causes axonal beading and localized cytoskeletal damage. Exp. Neurol. 212:422-430.

[17]. Jordan, M. A., and L. Wilson. 2004. Microtubules as a target for anticancer drugs. Nat. Rev. Cancer. 4:253-265.

[18]. Bocquet, A., R. Berges, J. Eyer. 2009. Neurofilaments bind tubulin and modulate its polymerization. J. Neurosci. 29:11043-11054.

[19]. Kushkuley, J., W. K. Chan, T. B. Shea. 2009. Neurofilament crossbridging competes with kinesin-dependent association of neurofilaments with microtubules. J. Cell Sci. 122:3579-3586.

[20]. Mori, H., and M. Kurokawa. 1979. Purification of neurofilaments and their interaction with vinblastine sulfate. Cell Struct. Funct. 4:163-167.

[21]. Oblinger, M. M., S. T. Brady, R. J. Lasek. 1987. Cytotypic differences in the protein composition of the axonally transported cytoskeleton in mammalian neurons. J. Neurosci. 7:453-462.

[22]. Wagner, O. I., S. Rammensee, P. A. Janmey. 2007. Softness, strength and self-repair in intermediate filament networks. Exp. Cell Res. 313:2228-2235.

[23]. Janmey, P. A., and D. A. Weitz. 2004. Dealing with mechanics: mechanisms of force transduction in cells. Trends Biochem. Sci. 29:364-370.

[24]. Kasza, K. E., A. C. Rowat, D. A. Weitz. 2007. The cell as a material. Curr. Opin. Cell Biol. 19:101-107.

[25]. Bausch, A. R., and K. Kroy. 2006. A bottom-up approach to cell mechanics. Nat. Phys. 2:231-238.

[26]. Orr, A. W., B. P. Helmke, M. A. Schwartz. 2006. Mechanisms of mechanotransduction. Dev. Cell. 10:11-20.

[27]. Chien, S. 2007. Mechanotransduction and endothelial cell homeostasis: the wisdom of the cell. Am. J. Physiol. Heart Circ. Physiol. 292:H1209-H1224.

[28]. Geiger, B., and A. Bershadsky. 2002. Exploring the neighborhood: adhesion-coupled cell mechanosensors. Cell. 110:139-142.

[29]. Hoffman, B. D., and J. C. Crocker. 2009. Cell mechanics: dissecting the physical responses of cells to force. Annu. Rev. Biomed. Eng. 11:259-288.

[30]. Wang, J. T., Z. A. Medress, and B. A. Barres. 2012. Axon degeneration: molecular mechanisms of a self-destruction pathway. J. Cell Biol. 196:7-18. Biophysical Journal 103(3) 405-414 Mechanical Properties of Axons 413

[31]. Beirowski, B., A. No'gra'di, M. P. Coleman. 2010. Mechanisms of axonal spheroid formation in central nervous system Wallerian degeneration. J. Neuropathol. Exp. Neurol. 69:455-472.

[32]. Barrientos, S. A., N. W. Martinez, F. A. Court. 2011. Axonal degeneration is mediated by the mitochondrial permeability transition pore. J. Neurosci. 31:966-978.

[33]. Tang-Schomer, M. D., A. R. Patel, D. H. Smith. 2010. Mechanical breaking of microtubules in axons during dynamic stretch injury underlies delayed elasticity, microtubule disassembly, and axon degeneration. FASEB J. 24:1401-1410.

[34]. Lundborg, G., R. Myers, and H. Powell. 1983. Nerve compression injury and increased endoneurial fluid pressure: a "miniature compartment syndrome". J. Neurol. Neurosurg. Psychiatry. 46:1119-1124.

[35]. Dahlin, L. B., B. Rydevik, J. Sjo'strand. 1984. Changes in fast axonal transport during experimental nerve compression at low pressures. Exp. Neurol. 84:29-36.

[36]. Powell, H. C., and R. R. Myers. 1986. Pathology of experimental nerve compression. Lab. Invest. 55:91-100.

[37]. Keir, P. J., J. M. Bach, D. M. Rempel. 2007. Guidelines for wrist posture based on carpal tunnel pressure thresholds. Hum. Factors 49:88-99.

[38]. Ghajar, J. 2000. Traumatic brain injury. Lancet. 356:923-929.

[39]. Pierce, J. E., D. H. Smith, T. K. McIntosh. 1998. Enduring cognitive, neurobehavioral and histopathological changes persist for up to one year following severe experimental brain injury in rats. Neuroscience. 87:359-369.

[40]. Witt, A., and S. T. Brady. 2000. Unwrapping new layers of complexity in axon/glial relationships. Glia. 29:112-117.

[41]. Heimburg, T., and A. D. Jackson. 2005. On soliton propagation in biomembranes and nerves. Proc. Natl. Acad. Sci. USA. 102:9790-9795.

[42]. Andersen, S. S., A. D. Jackson, and T. Heimburg. 2009. Towards a thermodynamic theory of nerve pulse propagation. Prog. Neurobiol. 88:104-113.

[43]. Griesbauer, J., S. Bossinger, M. F. Schneider. 2012. Propagation of 2D pressure pulses in lipid monolayers and its possible implications for biology. Phys. Rev. Lett. 108:198103.

[44]. Abramoff, M. D., P. J. Magalhaes, and S. J. Ram. 2004. Image processing with Image J. Biophot. Int. 11:36-42.

[45] Grabrucker A, Vaida B, Bockmann J, Boeckers T M. Synaptogenesis of hippocampal neurons in primary cell culture. Cell Tissue Res. 2009, 338(3):333-41.

[46] Magdesian M H, Sanchez F S, Lopez M, Thostrup P, Durisic N, Belkaid W, Liazoghli D, Grüter P, Colman D R. Atomic force microscopy reveals important differences in axonal resistance to injury. Biophys J. 2012, 103(3):405-14.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A microfluidic device comprising:

first and second compartments fluidly connected by microchannels extending therebetween, the first compartment comprising:

a main chamber having an upper wall and opposite sidewalls;

a first auxiliary room having a first peripheral wall joined to the upper wall of the main chamber and to a respective one of the opposite sidewalls, the first peripheral wall defining a first opening connecting the first auxiliary room to the main chamber;

a second auxiliary room having a second peripheral wall, the second auxiliary room being located opposite the first auxiliary room with the main chamber extending therebetween;

wherein the upper wall of the main chamber and the respective one of the opposite sidewalls extend from the first peripheral wall to define a side portion of the main chamber that tapers outwardly away from the first opening and toward a center portion of the upper wall of the main chamber;

the microchannels comprising inlets opened to the main chamber and aligned along a microchannel inlet plane, and being distributed in a side-by-side relationship relative to the opposite sidewalls; and at least one of the opposite sidewalls intersecting with the microchannel inlet plane along an intersection line to form an angle ranging from 70° to 110° therewith.

2. The microfluidic device of claim 1, wherein the angle is between 80° and 100°.

3. The microfluidic device of claim 1, wherein the angle is between 85° and 95°.

4. The microfluidic device of claim 1, wherein the angle is about 90°.

5. The microfluidic device of claim 1, wherein the microchannels extend substantially parallelly relative to each other.

6. The microfluidic device of claim 1, wherein the upper wall of the main chamber of the first compartment is curved inwardly towards the microchannels to form a curved upper wall.

7. The microfluidic device of claim 1, further comprising a planar substrate positioned onto or underneath the microfluidic device to enclose the microchannels.

8. The microfluidic device of claim 7, wherein at least one of the planar substrate, the microchannels or the main chamber further comprises a coating promoting at least one of retention, adhesion, attachment and growth of cells.

9. The microfluidic device of claim 1, wherein the microchannels have a shape selected from the group consisting of a rectangular shape, a square shape, a triangular shape, a U-shape, and a V-shape.

10. The microfluidic device of claim 1, wherein the microchannels have a microchannel height equal or less than a main chamber height of the main chamber.

11. The microfluidic device of claim 1, wherein the microchannels have a microchannel height ranging from 1 µm to 250 µm.

12. The microfluidic device according of claim 1, wherein the microchannels have a microchannel length of at least 0.1 mm.

* * * * *